United States Patent
Washington et al.

(10) Patent No.: US 10,568,826 B2
(45) Date of Patent: Feb. 25, 2020

(54) SHAPING KERATIN FIBRES USING A PRETREATMENT AND A PROTEIN CROSSLINKING COMPOSITION

(71) Applicant: The Procter & Gamble Company, Cincinnati, OH (US)

(72) Inventors: Randy Purnell Washington, West Chester, OH (US); Andreas Flohr, Darmstadt (DE); Jamie Angel Reed, Maineville, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 135 days.

(21) Appl. No.: 14/972,993

(22) Filed: Dec. 17, 2015

(65) Prior Publication Data

US 2016/0175220 A1    Jun. 23, 2016

Related U.S. Application Data

(60) Provisional application No. 62/094,311, filed on Dec. 19, 2014.

(51) Int. Cl.
| | |
|---|---|
| *A61K 8/49* | (2006.01) |
| *A61Q 5/06* | (2006.01) |
| *A61K 8/60* | (2006.01) |
| *A61K 8/36* | (2006.01) |
| *A61K 8/898* | (2006.01) |
| *A61Q 5/12* | (2006.01) |
| *A45D 7/06* | (2006.01) |
| *A61K 8/64* | (2006.01) |
| *A61K 8/362* | (2006.01) |
| *A61Q 5/04* | (2006.01) |
| *A61K 8/365* | (2006.01) |

(52) U.S. Cl.
CPC ............. *A61K 8/4973* (2013.01); *A45D 7/06* (2013.01); *A61K 8/36* (2013.01); *A61K 8/362* (2013.01); *A61K 8/365* (2013.01); *A61K 8/4913* (2013.01); *A61K 8/60* (2013.01); *A61K 8/64* (2013.01); *A61K 8/898* (2013.01); *A61Q 5/04* (2013.01); *A61Q 5/06* (2013.01); *A61Q 5/12* (2013.01); *A61K 2800/30* (2013.01); *A61K 2800/596* (2013.01); *A61K 2800/884* (2013.01); *A61K 2800/95* (2013.01)

(58) Field of Classification Search
None
See application file for complete search history.

(56) References Cited

U.S. PATENT DOCUMENTS

| | | |
|---|---|---|
| 3,966,903 A | 6/1976 | Torii et al. |
| 4,148,329 A | 4/1979 | Jaskowski |
| 4,364,837 A | 12/1982 | Pader |
| 4,382,765 A | 5/1983 | Moller et al. |
| 4,387,765 A | 6/1983 | Kristoffersson |
| 4,602,143 A | 7/1986 | Mack et al. |
| 4,690,818 A | 9/1987 | Puchalski, Jr. et al. |
| 4,740,669 A | 4/1988 | Takimae |
| 4,795,629 A | 1/1989 | Siuta-Mangano |
| 4,812,307 A | 3/1989 | Siuta-Mangano |
| 4,960,771 A | 10/1990 | Rajadhyaksha |
| 5,110,318 A | 5/1992 | Altobelli et al. |
| 5,578,582 A | 11/1996 | Knutsen et al. |
| 5,578,682 A | 11/1996 | White |
| 5,641,477 A | 6/1997 | Syed et al. |
| 5,858,179 A | 1/1999 | Loda |
| 6,248,979 B1 | 6/2001 | Cafaro |
| 6,255,332 B1 | 7/2001 | Philippe |
| 6,354,305 B1 | 3/2002 | Janouch et al. |
| 6,363,215 B1 | 3/2002 | Cafaro |
| 6,423,942 B1 | 7/2002 | Liao |
| 6,472,478 B1 | 10/2002 | Funk et al. |
| 6,486,105 B1 | 11/2002 | Cannell et al. |
| 6,488,920 B1 | 12/2002 | Thomas |
| 7,521,926 B2 | 4/2009 | Beck et al. |
| 7,550,136 B2 | 6/2009 | Warner et al. |
| 7,699,058 B1 | 4/2010 | Jay |
| 7,815,900 B1 | 10/2010 | Cannell et al. |
| 8,035,061 B2 | 10/2011 | Jung |
| 8,192,728 B2 | 6/2012 | Paul |
| 8,230,868 B2 | 7/2012 | Choi |
| 8,286,645 B2 | 10/2012 | Kyu et al. |
| 8,349,780 B2 | 1/2013 | Baker |
| 8,424,543 B2 | 4/2013 | Lombardi et al. |
| 8,513,200 B2 | 8/2013 | Dixon |
| 8,883,710 B2 | 11/2014 | Willey |
| 9,414,999 B2 | 8/2016 | Paul et al. |
| 9,415,000 B2 | 8/2016 | Washington et al. |
| 9,713,369 B2 | 7/2017 | Washington et al. |

(Continued)

FOREIGN PATENT DOCUMENTS

| | | |
|---|---|---|
| CN | 201504727 U | 6/2010 |
| DE | 19812669 A1 | 10/1999 |

(Continued)

OTHER PUBLICATIONS

ThermoScientific <https://tools.thermofisher.com/content/sfs/manuals/MAN0011369_BM_PEG2_BM_PEG3_UG.pdf> available Feb. 28, 2006; accessed May 1, 2016.*

(Continued)

*Primary Examiner* — Nicole P Babson
(74) *Attorney, Agent, or Firm* — Alexandra S. Anoff

(57) ABSTRACT

Described herein is a method for shaping keratin fibers including providing a pretreatment composition which includes a pretreatment active agent; applying the pretreatment composition to keratin fibers; leaving the pretreatment composition on the keratin fibers for a time period from about 5 minutes to about 24 hours; providing a crosslinking composition including from about 1% to about 20% of one or more protein crosslinking agents and a cosmetically acceptable carrier; applying the crosslinking composition to keratin fibers; and mechanically shaping the keratin fibers with an appliance at a temperature of from about 50° C. to about 280° C.

15 Claims, No Drawings

(56) References Cited

U.S. PATENT DOCUMENTS

| | | |
|---|---|---|
| 9,781,988 B2 | 10/2017 | Washington |
| 9,872,824 B2 | 1/2018 | Kadir et al. |
| 9,956,155 B2 | 5/2018 | Washington |
| 10,064,799 B2 | 9/2018 | Washington |
| 10,195,130 B2 | 2/2019 | Washington |
| 10,434,051 B2 | 10/2019 | Washington |
| 2001/0013513 A1 | 8/2001 | Chan |
| 2002/0157682 A1 | 10/2002 | Ueyama et al. |
| 2004/0000319 A1 | 1/2004 | Carballada et al. |
| 2004/0011373 A1 | 1/2004 | Tsuchiya et al. |
| 2004/0043046 A1 | 3/2004 | Vic et al. |
| 2004/0156800 A1 | 8/2004 | Brun et al. |
| 2004/0206368 A1 | 10/2004 | Warner et al. |
| 2005/0018283 A1 | 1/2005 | Kimura |
| 2005/0048018 A1* | 3/2005 | Fadeeva ............... A61K 8/60 424/70.13 |
| 2005/0058618 A1 | 3/2005 | Evans |
| 2005/0136019 A1 | 6/2005 | Malle et al. |
| 2005/0196369 A1* | 9/2005 | Ueyama ............... A61K 8/35 424/70.2 |
| 2005/0214239 A1 | 9/2005 | Nojiri et al. |
| 2006/0035807 A1 | 2/2006 | Kasturi et al. |
| 2006/0124625 A1 | 6/2006 | Keig |
| 2006/0196523 A1 | 9/2006 | Choi |
| 2006/0257344 A1 | 11/2006 | Nguyen et al. |
| 2007/0028938 A1 | 2/2007 | Tiwari |
| 2007/0106347 A1 | 5/2007 | Lin |
| 2007/0119844 A1 | 5/2007 | Lo et al. |
| 2008/0075682 A1 | 3/2008 | Cassier |
| 2008/0275532 A1 | 11/2008 | Yamazaki |
| 2009/0118421 A1 | 5/2009 | Falk |
| 2009/0126756 A1 | 5/2009 | Syed et al. |
| 2009/0145452 A1 | 6/2009 | Anderson et al. |
| 2009/0155198 A1 | 6/2009 | Vic et al. |
| 2009/0283106 A1 | 11/2009 | Torgerson et al. |
| 2009/0285768 A1* | 11/2009 | Baker ............... A61K 8/361 424/59 |
| 2009/0320869 A1 | 12/2009 | Fadeeva |
| 2010/0006116 A1 | 1/2010 | Bell |
| 2010/0037909 A1 | 2/2010 | Gross |
| 2010/0089413 A1 | 4/2010 | Wright et al. |
| 2010/0101598 A1 | 4/2010 | Ng et al. |
| 2010/0132733 A1 | 6/2010 | Kyu et al. |
| 2010/0192970 A1 | 8/2010 | Takahashi et al. |
| 2010/0247800 A1 | 9/2010 | Willey et al. |
| 2010/0269848 A1 | 10/2010 | Morgandi et al. |
| 2010/0300471 A1 | 12/2010 | Malle et al. |
| 2010/0310491 A1* | 12/2010 | Falk ............... A61K 8/06 424/70.122 |
| 2011/0008265 A1 | 1/2011 | Anderson et al. |
| 2011/0017227 A1 | 1/2011 | Samain |
| 2011/0020627 A1 | 1/2011 | Falk et al. |
| 2011/0114108 A1 | 5/2011 | Baker et al. |
| 2011/0120491 A1 | 5/2011 | You |
| 2011/0253164 A1 | 10/2011 | Morgandi et al. |
| 2011/0256083 A1 | 10/2011 | Smith |
| 2011/0256084 A1 | 10/2011 | Dixon |
| 2012/0192887 A1 | 8/2012 | Vic et al. |
| 2012/0213723 A1 | 8/2012 | Nguyen et al. |
| 2012/0291797 A1 | 11/2012 | deGrood et al. |
| 2012/0312317 A1* | 12/2012 | Mannozzi ............... A61Q 5/06 132/206 |
| 2013/0118520 A1 | 5/2013 | Mannozzi |
| 2013/0192625 A1 | 8/2013 | Migliori et al. |
| 2013/0276809 A1 | 10/2013 | Wood |
| 2013/0298933 A1 | 11/2013 | Malle et al. |
| 2013/0299390 A1 | 11/2013 | Koczo et al. |
| 2013/0315852 A1 | 11/2013 | Streuli |
| 2013/0319449 A1 | 12/2013 | Xavier et al. |
| 2013/0340785 A1 | 12/2013 | Baum et al. |
| 2014/0090660 A1 | 4/2014 | Xavier et al. |
| 2014/0190507 A9 | 7/2014 | Xavier et al. |
| 2014/0196741 A1 | 7/2014 | Cabourg |
| 2014/0230842 A1 | 8/2014 | Parris et al. |
| 2014/0235885 A1 | 8/2014 | Koczo et al. |
| 2015/0007876 A1 | 1/2015 | Komai et al. |
| 2015/0020838 A1 | 1/2015 | Kamath et al. |
| 2015/0034119 A1 | 2/2015 | Pressly |
| 2015/0040936 A1 | 2/2015 | Baghdadli et al. |
| 2015/0096584 A1 | 4/2015 | Washington |
| 2015/0128983 A1 | 5/2015 | Vic et al. |
| 2015/0128984 A1 | 5/2015 | Paul et al. |
| 2015/0157561 A1 | 6/2015 | De Graaff |
| 2015/0173478 A1 | 6/2015 | Adams |
| 2015/0173479 A1 | 6/2015 | Adams |
| 2015/0173480 A1 | 6/2015 | Washington |
| 2015/0174023 A1 | 6/2015 | Washington et al. |
| 2015/0174027 A1 | 6/2015 | Washington et al. |
| 2015/0174028 A1 | 6/2015 | Washington et al. |
| 2015/0174029 A1 | 6/2015 | Washington et al. |
| 2015/0174030 A1 | 6/2015 | Washington et al. |
| 2015/0174031 A1 | 6/2015 | Washington et al. |
| 2015/0174032 A1 | 6/2015 | Washington et al. |
| 2015/0174035 A1 | 6/2015 | Reed |
| 2015/0174036 A1 | 6/2015 | Washington et al. |
| 2015/0174037 A1 | 6/2015 | Washington et al. |
| 2015/0174432 A1 | 6/2015 | Adams |
| 2015/0174793 A1 | 6/2015 | Adams |
| 2015/0328102 A1* | 11/2015 | Pressly ............... A61Q 5/08 424/70.1 |
| 2015/0374604 A1 | 12/2015 | Kadir |
| 2016/0008243 A1 | 1/2016 | Paul |
| 2016/0158138 A1 | 6/2016 | Baum et al. |
| 2016/0175218 A1 | 6/2016 | Washington et al. |
| 2016/0175219 A1 | 6/2016 | Washington et al. |
| 2016/0175220 A1 | 6/2016 | Washington et al. |
| 2016/0296449 A1 | 10/2016 | Kadir et al. |
| 2016/0317415 A1 | 11/2016 | Washington et al. |
| 2016/0367451 A1 | 12/2016 | Washington |
| 2016/0367459 A1 | 12/2016 | Washington et al. |
| 2017/0035193 A1 | 2/2017 | Vecchiola |
| 2017/0181516 A1 | 6/2017 | Washington et al. |

FOREIGN PATENT DOCUMENTS

| | | |
|---|---|---|
| DE | 102005059936 A1 | 10/2006 |
| EP | 1903034 A1 | 3/2008 |
| EP | 2111852 A2 | 10/2009 |
| FR | 2950247 B1 | 2/2012 |
| FR | 3006585 B1 | 5/2015 |
| GB | 1376136 A | 12/1974 |
| JP | 3629400 B2 | 3/2005 |
| JP | 2007176826 A | 7/2007 |
| JP | 4950487 B2 | 6/2012 |
| JP | 2013234149 A | 11/2013 |
| KR | 2020060028353 | 9/2007 |
| WO | WO02078655 A2 | 10/2002 |
| WO | WO2004043330 A2 | 5/2004 |
| WO | WO2009045556 A1 | 4/2009 |
| WO | WO2010049623 A2 | 5/2010 |
| WO | WO2010067323 A1 | 6/2010 |
| WO | WO2011074143 A1 | 6/2011 |
| WO | WO2011089985 A1 | 7/2011 |
| WO | WO2012027369 A2 | 3/2012 |
| WO | WO2013092959 A1 | 6/2013 |
| WO | WO2013098332 A2 | 7/2013 |
| WO | WO2013117770 A2 | 8/2013 |
| WO | WO2013117843 A1 | 8/2013 |
| WO | WO2013142497 A1 | 9/2013 |
| WO | WO2014001540 A2 | 1/2014 |
| WO | WO2014016658 A1 | 1/2014 |

OTHER PUBLICATIONS

New World Encyclopedia. "Keratin" <http://www.newworldencyclopedia.org/entry/Keratin>; available Sep. 19, 2008; accessed May 1, 2016.*

Ajinomoto. http://www.ajichem.com/en/products/amino-acids.aspx. Published: Dec. 3, 2008.

All final and non-final office actions for U.S. Appl. No. 14/508,310.

All final and non-final office actions for U.S. Appl. No. 14/576,820.

All final and non-final office actions for U.S. Appl. No. 14/576,866.

(56) References Cited

OTHER PUBLICATIONS

All final and non-final office actions for U.S. Appl. No. 14/576,937.
All final and non-final office actions for U.S. Appl. No. 14/576,970.
All final and non-final office actions for U.S. Appl. No. 14/577,003.
All final and non-final office actions for U.S. Appl. No. 14/577,042.
All final and non-final office actions for U.S. Appl. No. 14/577,100.
All final and non-final office actions for U.S. Appl. No. 14/577,135.
All final and non-final office actions for U.S. Appl. No. 14/577,186.
All final and non-final office actions for U.S. Appl. No. 14/675,903.
All final and non-final office actions for U.S. Appl. No. 14/972,926.
All final and non-final office actions for U.S. Appl. No. 14/972,966.
All final and non-final office actions for U.S. Appl. No. 15/185,419.
All final and non-final office actions for U.S. Appl. No. 15/185,439.
All final and non-final office actions for U.S. Appl. No. 15/206,595.
All final and non-final office actions for U.S. Appl. No. 15/456,632.
Bobbio. Cienc. Tecnol. Aliment, vol. 20, No. 3, Campas Sep.-Dec. 2003.
Brazil Fabulous. https://web.archieve.org/web/20100402084028/http://brazillianfab.wordpress.com/the-brazilian-keratin-clinic/your-keratin-questions-answered/. Published Apr. 2, 2010.
Brazilian Blowout Zero. http://icanhassscience.com/chemistry/brazilian-blowouts-new-formula-sans-methylene-glycol/. Published Feb. 14, 2011.
Brazilian Keratin. http://www.verticalsinhair.com/index.php?option=com_content&view=category&layout=blow&id=43. Published 2010.
Edible Medicinal and Non-Medicinal Plants. vol. 3. Lim. Copyright: 2012, p. 634.
National Center for Biotechnology Information. PubChem Compound Database: CID-1045, https://pubchem.ncbi.nlm.nih.gov/compound/1045 (accessed Aug. 4, 2016).
PCT International Search Report and Written Opinion for PCT/US2014/058777 dated Jan. 19, 2015.
PCT International Search Report and Written Opinion for PCT/US2014/066627 dated Feb. 18, 2015.
PCT International Search Report and Written Opinion for PCT/US2014/069056 dated Mar. 17, 2015.
PCT International Search Report and Written Opinion for PCT/US2014/069057 dated Mar. 17, 2015.
PCT International Search Report and Written Opinion for PCT/US2014/069059 dated Mar. 19, 2015.
PCT International Search Report and Written Opinion for PCT/US2014/069061 dated Mar. 18, 2015.
PCT International Search Report and Written Opinion for PCT/US2014/069450 dated Mar. 17, 2015.
PCT International Search Report and Written Opinion for PCT/US2014/069451 dated Apr. 21, 2015.
PCT International Search Report and Written Opinion for PCT/US2014/071436 dated Apr. 9, 2015.
PCT International Search Report and Written Opinion for PCT/US2014/071455 dated Apr. 9, 2015.
PCT International Search Report and Written Opinion for PCT/US2015/065670 dated Mar. 31, 2016.
PCT International Search Report and Written Opinion for PCT/US2015/065673 dated Mar. 10, 2016.
PCT International Search Report and Written Opinion for PCT/US2016/037959 dated Sep. 19, 2016.
PCT International Search Report and Written Opinion for PCT/US2016/037961 dated Sep. 21, 2016.
Reiger, Martin M. (2000), Harry's Cosmeticology, vols. I-11 (8th Edition). Chemical Publishing Company Inc. Online version available at http://app.knovel.com/hotlink/toc/id:kpHCVIIIEH/harrys-cosmeticology.
Tuliao Gongye, vol. 39, Issue8, pp. 15-19, 23, Journal (Chinese) 2009.
Whole World Botanicals, http://wholeworldbotanicals.com/camu-camu-myrciaria-dubia/. Published Mar. 1, 2003.
Fanci-full. https://web.archive.org/web/20101018033411/https://fanci-fullhair.com/fanci/how to use.html. Published: Oct. 18, 2010.
PCT International Search Report and Written Opinion for PCT/US2015/065674 dated Mar. 14, 2016.

\* cited by examiner

1

SHAPING KERATIN FIBRES USING A PRETREATMENT AND A PROTEIN CROSSLINKING COMPOSITION

FIELD OF THE INVENTION

A method for shaping keratin fibres comprising providing and applying a pretreatment composition including a pretreatment active agent selected from the group consisting of maleic anhydride, maleic acid, citric acid, fumaric acid, and mixtures thereof. The method also comprises providing a crosslinking composition, wherein the crosslinking composition comprises a protein crosslinking agent and a cosmetically acceptable carrier; applying the crosslinking composition to keratin fibres and mechanically shaping the keratin fibres.

BACKGROUND OF THE INVENTION

Consumers are constantly demanding products that meet their daily styling and conditioning needs without damaging the hair. The perceived and sometimes real impact of various treatments and the implements such as blow drying and flat iron can have detrimental effects on the acute and chronic nature of hair.

Permanent methods—or relaxers—usually comprise the steps of applying onto hair a composition comprising a high pH solution (or combination of components to generate high pH), leaving on for a protracted time and then applying a neutralizing composition. A relaxer is a treatment predominately used by people of African-descent to permanently straighten hair. The treatment relies on either the one-step sodium hydroxide (lye) or a two step (e.g. guanidine carbonate and calcium hydroxide) to achieve very high pH (pH 12-14).

Semi-permanent benefits can be achieved using redox chemistry such as thioglycolic acid (TGA) and hydrogen peroxide. Here, the curly hair is transformed into the straight hair because the disulfide bonds are broken by the reaction with TGA. The straighter style is locked in during the oxidation step with hydrogen peroxide.

Non-permanent methods usually comprise the step of heating the hair with a flat-iron or heating element. Methods using such devices in combination with chemically-modifying the internal hair fibres can obtain long-lasting effects e.g. over several months. The Brazilian Keratin Treatments (BKTs) enable the achievement of a straight hairstyle that lasts several months via a shampoo treatment. The key active in BKTs is formaldehyde. The most efficacious treatments (used mainly in salons) rely on high temperature— usually 232° C. (450° F.)—with formaldehyde. Hair treated with products with high concentration of formaldehyde such as Brazilian Blowout delivers semi-permanent straight hair. Over time and following shampooing, the hair reverts back to a curly configuration.

The known methods for straightening hair all have drawbacks. The permanent methods are typically time-consuming and may damage hair. In addition, such methods show little flexibility so that any need and/or wish for changing the hairstyle would require conducting again a "permanent" wave onto hair, which is time-consuming and further damages the hair.

Along with the high potential skin irritation during application, relaxers tend to permanently change the hair by breaking the natural disulfide bonds in the hair. This leaves the hair weaker and more prone for further breakage. Overprocessing can also increase hair damage and skin irritation. Consumer products using redox chemistry to achieve semi-permanent benefits, but overprocessing the hair and the strong sulphur smell are concerns of technologies based on reducing chemistry.

According to the US National Toxicology Program, formaldehyde is known to be a human carcinogen. Therefore, providing a semi-permanent style with carcinogen-free formulation is paramount. Given the safety concern of formaldehyde and the damaging effect of relaxers and reducing chemistry, there is a need for a safe alternative to durable straightening that does not break disulfide bonds.

None of the above methods allow achieving a hairstyle that may be retained and/or recovered after at least one shampoo treatment without severely damaging the hair or using a carcinogenic active. There is a need for the provision of a method for achieving a hairstyle that lasts at least five shampoo treatments so that the user would not need to re-shape hair after each shampoo but would still have the opportunity to change hairstyle after some time and without needing to use stringent or harsh hair treatment, such as the permanent technologies outlined above.

Accordingly, there is a need therefore for providing a method for achieving and semi-permanently retaining and/or recovering hairstyle using actives that do not break disulfide bonds (reducing agents) or that are considered carcinogenic. There is also the need for providing a method for obtaining a hairstyle exhibiting resistance to shampoo treatments. Particularly, there is a need for providing a method for retaining and/or recovering hairstyle after at least one shampoo treatment, particularly after five shampoo treatments, more particularly after ten shampoo treatments. In addition, there is a need for providing a method for achieving and retaining and/or recovering hairstyle, without damaging hair. Also, there is a need for providing more economic semi-permanent hair straightening or hair relaxing treatments.

SUMMARY OF THE INVENTION

Described herein is a method for shaping keratin fibres comprising (a) providing a pretreatment composition, wherein the pretreatment composition comprises a pretreatment active agent, wherein the pretreatment active agent is selected from the group consisting of maleic anhydride, maleic acid, citric acid, fumaric acid, and mixtures thereof; (b) applying the pretreatment composition to keratin fibers; (c) leaving the pretreatment composition on the keratin fibers for a time period from about 5 minutes to about 24 hours; (d) providing a crosslinking composition, wherein the crosslinking composition comprises: (1) from about 1% to about 20% of one or more protein crosslinking agents; and (2) a cosmetically acceptable carrier; (e) applying the crosslinking composition to keratin fibres; and (f) mechanically shaping the keratin fibres with an appliance at a temperature of from about 50° C. to about 280° C.

These and other features, aspects, and advantages of the present invention will become evident to those of ordinary skill in the art from a reading of the present disclosure.

DETAILED DESCRIPTION OF THE INVENTION

Definitions and General

In this document, including in all embodiments of all aspects of the present invention, the following definitions apply unless specifically stated otherwise. All percentages are by weight of the total composition. All ratios are weight ratios. References to 'parts' e.g. a mixture of 1 part X and 3 parts Y, is a ratio by weight. "QS" or "QSP" means sufficient quantity for 100% or for 100 g. +/− indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 25° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International. Herein: "min" means "minute" or "minutes"; "mol" means mole; "nanometers" is abbreviated "nm"; "g" following a number means "gram" or "grams". All weights as they pertain to listed ingredients are based on the active level and do not include carriers or by-products that may be included in commercially available materials. Herein, "comprising" means that other steps and other ingredients can be in addition. "Comprising" encompasses the terms "consisting of" and "consisting essentially of". The compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In at least one embodiment" means that one or more embodiments, optionally all embodiments or a large subset of embodiments, of the present invention has/have the subsequently described feature. Where amount ranges are given, these are to be understood as being the total amount of said ingredient in the composition, or where more than one species fall within the scope of the ingredient definition, the total amount of all ingredients fitting that definition, in the composition. For example, if the composition comprises from about 1% to about 5% fatty alcohol, then a composition comprising 2% stearyl alcohol and 1% cetyl alcohol, would fall within the scope.

"Molecular weight" or "M.Wt." or "MW" and grammatical equivalents mean the number average molecular weight.

"Viscosity" is measured at 25° C. using a HAAKE Rotation Viscometer VT 550 with cooling/heating vessel and sensor systems according to DIN 53019 at a shear rate of 12.9 s$^{-1}$.

"Water-soluble" refers to any material that is sufficiently soluble in water to form a clear solution to the naked eye at a concentration of 0.1% by weight of the material in water at 25° C. The term "water-insoluble" refers to any material that is not "water-soluble".

"Substantially free from" or "substantially free of" means less than about 1%, or less than 0.8%, or less than 0.5%, or less than 0.3%, or about 0%, by total weight of the composition or formulation.

"Keratin fibres" means fibrous material composed of keratin. "Hair" means mammalian keratin fibres including scalp hair, facial hair, eyelashes, and body hair. It includes such hair still being attached to a living subject and also hair that has been removed therefrom such as hair swatches and hair on a doll/mannequin. In at least one embodiment, "hair" means human hair. "Hair shaft" or "hair fibre" means an individual hair strand and may be used interchangeably with the term "hair." "Cosmetically acceptable" means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives" includes but is not limited to, amide, ether, ester, amino, carboxyl, acetyl, acid, salt and/or alcohol derivatives of a given compound. In at least one embodiment, "derivatives thereof" means the amide, ether, ester, amino, carboxyl, acetyl, acid, salt and alcohol derivatives.

"Monomer" means a discrete, non-polymerised chemical moiety capable of undergoing polymerisation in the presence of an initiator or any suitable reaction that creates a macromolecule e.g. such as polycondensation, polyaddition, anionic or cationic polymerization. "Unit" means a monomer that has already been polymerised i.e. is part of a polymer.

"Polymer" means a chemical formed from the polymerisation of two or more monomers. The term "polymer" shall include all materials made by the polymerisation of monomers as well as natural polymers. Polymers made from only one type of monomer are called homopolymers. Herein, a polymer comprises at least two monomers. Polymers made from two or more different types of monomers are called copolymers. The distribution of the different monomers can be random, alternating or block-wise (i.e. block copolymer). The term "polymer" used herein includes any type of polymer including homopolymers and copolymers.

"Kit" means a package comprising a plurality of components. "Kit" may be referred to as "kit-of-parts". An example of a kit is, for example, a first composition and a separately packaged second composition and optionally application instructions.

Description

The method described herein relates inter alia to a method for shaping keratin fibres. The present method allows the achievement of a semi-permanent hairstyle i.e. a durable hairstyle, and semi-permanent shaping of eyelashes. This semi-permanent hairstyle is retained after at least one shampoo treatment, particularly after five shampoo treatments, more particularly after 10 shampoo treatments. Besides the increased durability of the hairstyle, this method prevents clumping of hair and/or improves post-shampoo detangling of hair and feel. In addition, the inventors have found that this method increases the water- and humidity-resistance of the shape, increases the ease of style and/or increases the manageability of the shape after shampooing. Without wishing to be bound by any theory, it is believed that the above benefits are due to the steps conducted, their sequence, as well as the specific components used including the active agent. It is believed that the selected active agent diffuses into the shaft of the keratin fibre, reacts with amino groups in the keratin polypeptide and crosslinks these functional groups in the keratin protein structure, providing sufficient crosslinks to overcome the innate restoring force of the keratin fibre structure. Without wishing to be bound by theory, it is further believed that the pretreatment composition crosslinks with the hydroxyl or amino groups present in the protein crosslinking agent which has penetrated into the hair. This results in a durable shaping of keratin fibres, for example a durable hairstyle or durable eyelash shape.

The details of the different aspects of the invention are described hereinafter. The present invention relates inter alia to a method for shaping keratin fibres. The method comprises providing a pretreatment composition and a crosslinking composition.

Pretreatment Composition

The pretreatment composition comprises a pretreatment active agent selected from the group consisting of maleic anhydride, maleic acid, fumaric acid, citric acid, and mixtures thereof. The pretreatment composition may comprise about 0.1% to about 40%, or from about 0.5% to about 20%, or from about 1% to about 15%, or from about 7% to about 20%, or from about 8% to about 19%, or from about 10% to about 18%, or from about 4% to about 6%, or about 5% of the pretreatment active agent.

In at least one embodiment, the pretreatment composition comprises from about 7% to about 20%, or from about 8% to about 19%, or from about 10% to about 18% active agent. In at least one embodiment, the pretreatment composition comprises from about 12% to about 18% active agent.

In at least one embodiment, the preatment composition has a pH from about 2 to about 7, or from pH of about 4 to about 6, or from pH of about 5 to about 6.

In at least one embodiment, the pretreatment composition further comprises one or more cosmetic agents, including but not limited to: buffering agents, conditioning agents, emulsifying agents, cosmetically acceptable carriers, antioxidants, chelating agents, surfactants, hair styling polymers, and preservatives.

Crosslinking Composition

In an embodiment, the crosslinking composition is separate from the pretreatment composition. The crosslinking composition comprises a protein crosslinking agent, wherein the crosslinking agent is useful for reacting with and providing crosslinks in keratin.

In at least one embodiment, the crosslinking composition comprises from about 0.1% to about 40% crosslinking agent. In at least one embodiment, the composition comprises from about 1% to about 20%, or from about 0.1% to about 15%, or from about 1% to about 12%, or from about 2% to about 10% crosslinking agent.

In an embodiment, the hair shaping method described herein comprises applying a crosslinking composition to keratin fibres, wherein the crosslinking composition comprises a protein crosslinking agent, wherein the crosslinking agent has at least two functional groups selected from the group consisting of: —$NH_2$, —NH—, —SH, —OH, —C(=O)H, —C=O, and COOH; and wherein the crosslinking agent has a molecular weight of 500 g/mol or less. In at least one embodiment, the crosslinking agent has a molecular weight of 400 g/mol or less. In at least one embodiment, the crosslinking agent has a molecular weight of 300 g/mol or less, or from about 50 g/mol to 250 g/mol, or from about 80 g/mol to about 150 g/mol. The molecular weight is useful in view of penetration into the keratin fibers to crosslink it from the inside and not just superficially where the crosslink is more exposed to external factors. In the context of keratin fibres, the molecular weight is useful for penetration into the hair shaft i.e. under the cuticle.

In at least one embodiment, the crosslinking agent is liquid at 25° C. Crosslinking agents being liquid at this temperature have the advantage of providing improved hair feel versus crosslinking agents that are solid at this temperature.

In at least one embodiment, the crosslinking agent is capable of crosslinking keratin. In at least one embodiment, the crosslinking agent is selected from the group consisting of: diols, carboxylic acids, amines, diamines, reducing sugars, carbonyls, carboxylic acids, and mixtures thereof. In at least one embodiment, the crosslinking agent comprises at least two reactive sites selected from the functional groups consisting of: aldehyde, hydroxyl, carboxyl, and combinations thereof. In at least one embodiment, the crosslinking agent is selected from the group consisting of: 1,7-diaminoheptane, 1,4-diaminobutane, 6-aminohexan-1-ol, 6-amino hexanoic acid, 2-aminoacetic acid, 2-amino-2-oxo-ethanoic acid, 4-aminobutanoic acid, ribose, arabinose, xylose, lyxose, galactose, mannose, 3-(2-hydroxyethyl)-2-oxazolidinone, hexane-2,5-dione, butane-2,3-dione, ethanedial, 2-hydroxy-butanedial, 4-oxo-pentanoic acid, 1,4-butanediol, 1,6-hexanediol, 1,2,4-butanetriol, 1,2,6-hexanetriol, butanedioic acid, heptanedioic acid, oxoethanoic acid, 2,2-dihydroxyethanoic acid, 2,2'-oxybis(2-hydroxy)-ethanoic acid, 2-hydroxypropane-1,2,3-tricarboxylic acid, 1,2,3,4-butanetetracarboxylic acid, 1,3-dioxolan-2-one, dimethyl carbonate, diethyl carbonate, diphenyl carbonate; 1,3-dioxan-2-one, 4-methyl-1,3-dioxolan-2-one, and mixtures thereof. In at least one embodiment, the crosslinking agent is selected from the group consisting of: ribose, arabinose, oxoethanoic acid, 2,2-dihydroxyethanoic acid, 2-hydroxypropane-1,2,3-tricarboxylic acid, 1,2,3,4-butanetetracarboxylic acid, 1,2-bis(2maleimidoethoxy)ethane (CAS#115587-84-7), 3-dioxolan-2-one, and mixtures thereof.

In at least one embodiment, the crosslinking composition comprises a crosslinking agent, wherein the crosslinking agent is an amine or diamine Amines are useful because they are often naturally-derived (e.g. glycine), which is preferred by consumers versus synthetic compounds. This is not only for perceived health and lack of sensitisation reasons, but also for sustainability and environmental reasons—amines usually break down naturally and quickly and do not require special disposal methods. Also, amines are normally liquid at 25° C., which is useful from a feel perspective—consumers when touching their keratin fibres feel reduced roughness and friction versus actives being solid at 25° C. In at least one embodiment, the crosslinking agent is liquid at 25° C. The crosslinking agent is an amine or diamine; wherein the crosslinking agent has at least two functional groups selected from the group consisting of: —$NH_2$, —NH—, —SH, —OH, —C(=O)H, —C=O, —SH, and COOH; and wherein the crosslinking agent has a molecular weight of 500 g/mol or less. In at least one embodiment, the crosslinking agent has a molecular weight of 400 g/mol or less, or 300 g/mol or less, or from about 50 g/mol to 250 g/mol, or from about 80 g/mol to about 150 g/mol. The molecular weight is useful in view of penetration into the keratin fibers to crosslink it from the inside and not just superficially where the crosslink is more exposed to external factors. In the context of keratin fibres, the molecular weight is useful for penetration into the hair shaft i.e. under the cuticle.

In at least one embodiment, the crosslinking agent is a primary or secondary amine Amines usually include an organic species bearing at least one nitrogen atom as part of a functional group Amines may be mono-amines bearing one functional group comprising at least one nitrogen atom, diamines bearing two functional groups each comprising at least one nitrogen atom or polyamines bearing more than two functional groups each comprising at least one nitrogen atom. In a primary amine the nitrogen atom bears two hydrogen atoms and one organic moiety. In a secondary amine in which the nitrogen atom bears one hydrogen atoms and two organic moieties. In at least one embodiment, the organic moiety or moieties is/are independently selected from the group consisting of: $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ hydroxy, $C_1$-$C_{32}$ alkoxy, $C_1$-$C_{32}$ substituted alkoxy, $C_1$-$C_{32}$ alkylamino, and $C_1$-$C_{32}$ substituted alkylamino, —OH, —$NH_2$, and =NH.

In at least one embodiment, the crosslinking agent comprises at least one further functional group. In at least one embodiment, the further functional group is any organic moiety comprising at least one of an Oxygen, Nitrogen, Phosphorous, Boron or Sulfur atom. In at least one embodiment, the further functional group is selected from the group consisting of: Hydroxyl, Carbonyl, Aldehyde, Haloformyl, Carbonate ester, Carboxylate, Carboxyl, Ester, Methoxy, Hydroperoxy, Peroxy, Ether, Hemiacetal, Hemiketal, Acetal, Ketal, Orthoester, Orthocarbonate ester, Carboxamide, Primary amine, Secondary amine, Tertiary amine, Ammonium, Primary ketimine, Secondary ketimine, Primary aldimine, Secondary aldimine, Imide, Azide, Azo or Diimide, Cyanate, Isocyanate, Nitrate, Nitrile, Isonitrile, Nitrosooxy, Nitro, Nitroso, Pyridyl, Sulfhydryl, Sulfide, Disulfide, Sulfinyl, Sulfonyl, Sulfino, Sulfo, Thiocyanate, Isothiocyanate, Carbonothioyl, Carbonothioyl, Phosphino, Phosphono, Phosphate, Borono, Boronate, Borino, Borinate. In at least one embodiment, the crosslinking agent is a polyamine.

In at least one embodiment, the crosslinking agent is a diamine. In at least one embodiment, the crosslinking agent is a diamine conforming to the formula $H_2N$—$(CH_2)n$-$NH_2$, wherein n is an integer from 3 to 12, and isomers thereof. In at least one embodiment, the crosslinking agent is a diamine conforming to the formula $H_2N$—$(CH_2)n$-$NH_2$, wherein n is an integer from 2 to 12, or from 4 to 10, or from 5 to 8, and isomers thereof. 2-methylpropane-1,3-diamine is isomer of 1,4-diaminobutane. In at least one embodiment, the crosslinking agent is selected from the group consisting of: 1,7-diaminoheptane, 1,4-diaminobutane, 6-aminohexan-1-ol, 6-amino hexanoic acid, 2-aminoacetic acid, 2-amino-2-oxo-ethanoic acid, 4-aminobutanoic acid, and mixtures thereof. In at least one embodiment, the crosslinking agent is a diamine and wherein the diamine is selected from the group consisting of: 1,2-diaminoethane, 1,3-diaminopropane, 2-methylpropane-1,3-diamine, 1,4-diaminobutane, 1,5-diaminopentane, 1,6-diaminohexane, 1,7-diaminoheptane, 1,8-diaminooctane, 1,9-diaminononane, 1,10-diaminodecane, and mixtures thereof. In at least one embodiment, the crosslinking agent is a diamine and wherein the diamine is selected from the group consisting of: 1,7-diaminoheptane, 1,4-diaminobutane, and mixtures thereof. 1,4-diaminobutane has a molecular weight of about 88 g/mol and 1,7-diaminoheptane has a molecular weight of about 130 g/mol. In at least one embodiment, the crosslinking agent comprises a thiol group. In at least one embodiment, the crosslinking agent is 2-aminoethanethiol.

In at least one embodiment, the crosslinking agent is a sugar. Sugars are useful because they are naturally-derived, which is preferred by consumers versus synthetic compounds. This is not only for perceived health and lack of sensitisation reasons, but also for sustainability and environmental reasons—sugars break down naturally and quickly and do not require special disposal methods. Furthermore, sugars are also easy to source and relatively inexpensive. The crosslinking agent has a molecular weight of 500 g/mol or less. In at least one embodiment, the crosslinking agent has a molecular weight of 300 g/mol or less, or from about 50 g/mol to 250 g/mol, or from about 80 g/mol to about 150 g/mol. The molecular weight is useful in view of penetration into the keratin fibers to crosslink it from the inside and not just superficially where the crosslink is more exposed to external factors. In the context of keratin fibres, the molecular weight is useful for penetration into the hair shaft i.e. under the cuticle. In at least one embodiment, the crosslinking agent is liquid at 25° C. Crosslinking agents being liquid at this temperature have the advantage of providing improved hair feel versus crosslinking agents that are solid at this temperature. In at least one embodiment, the crosslinking agent is a monosaccharide. In at least one embodiment, the sugar is a monosaccharide and wherein the fixing composition comprises from about 0.1% to about 40%, or from about 0.5% to about 20%, or from about 1% to about 15%, or from about 7% to about 20%, or from about 8% to about 19%, or from about 10% to about 18% monosaccharide. In at least one embodiment, the crosslinking agent is a pentose or a hexose.

In at least one embodiment, the fixing composition comprises a reducing sugar, where the fixing composition is heated to a temperature of 100° C., the composition comprises from about 1% to about 20% reducing sugar. In at least one embodiment, the fixing composition comprises a reducing sugar and wherein, where the fixing composition is heated to a temperature of 100° C., the fixing composition comprises from about 12% to about 18% reducing sugar. In at least one embodiment, the fixing composition comprises sucrose, a buffering agent and a cosmetically acceptable carrier; and wherein, where the fixing composition is heated to a temperature of 100° C., the fixing composition comprises from about 1% to about 20% reducing sugar. Sucrose is able to break down into reducing sugar following heating. In at least one embodiment, the fixing composition comprises a reducing sugar. In at least one embodiment, the fixing composition comprises from about 0.1% to about 20.0%, or from about 2% to about 15%, or from about 5% to about 12% reducing sugar. In at least one embodiment, the fixing composition comprises from about 12% to about 18% reducing sugar. In at least one embodiment, the fixing composition comprises a total amount of reducing sugar being from about 12% to about 18% reducing sugar.

In at least one embodiment, the crosslinking composition comprises a reducing sugar and a cosmetically acceptable carrier. As used herein, the expression "reducing sugar" means any sugar that either has an aldehyde group or is capable of forming an aldehyde group in solution through isomerism, and that gives a positive result in the Benedict's test. An aldehyde group is —C(=O)H. The Benedict's test involves employment of the Benedict's solution. The Benedict's solution is available from Aldrich as 'Benedict's Reagent', which comprises sodium carbonate, copper sulphate pentahydrate and 2,5-difluorotoluene. In the Benedict's test, 1 mL of Benedict's solution is added to a 20 mL of 5% aqueous solution comprising a dissolved test compound. Benedict's solution contains blue copper(II) ions ($Cu^{2+}$). The solution is heated to 80° C. for 15 min and the resulting colour change is noted. The cupric ion of the Benedict's solution is reduced to cuprous ion by the aldehyde of the sugar. A positive test is confirmed with a change in colour as cupric ions ($Cu^{2+}$) are converted to cuprous ions i.e. reduced to copper(I) ions ($Cu^+$). These are precipitated as red copper(I) oxide which is insoluble in water. The test is also designed for longer heating time and higher temperature to note any colour change. The solution may range in colour (with increasing amounts of reducing sugar) from green, through yellow and orange, to red. Any colour change away from blue suggest levels of reducing sugar. The wavelength will change with the colour.

TABLE 1

*Assessment of sugars using the Benedict's Test*

| Sugar | 80° C., 15 min | 100° C., 40 min |
| --- | --- | --- |
| Control (buffer solution*) | Negative | Negative |
| Ribose | Positive | Positive |
| Arabinose | Positive | Positive |
| Glucose | Positive | Positive |
| Fructose | Positive | Positive |
| Xylose | Positive | Positive |
| Sucrose | Negative | Positive |
| Methyl glucoside | Negative | Positive |

*Benedict's solution only.

In general, the Benedict's reagent is used as a test for the presence of reducing sugars. This includes all monosaccharides and many disaccharides, including lactose and maltose. Even more generally, Benedict's test will detect the presence of aldehydes, and alpha-hydroxy-ketones, including those that occur in certain ketoses. Thus, although fructose, a ketose, is not strictly a reducing sugar, it is an alpha-hydroxy-ketone, it gives a positive test because it is converted to the aldoses glucose and mannose by the base in the reagent. The copper sulphate in Benedict's solution reacts with reducing sugars. One liter of Benedict's reagent can be prepared from 100 g of anhydrous sodium carbonate, 173 g of sodium citrate and 17.3 g of copper(II) sulfate pentahydrate. Benedict's Reagent provides a quantitative test for reducing sugars along with qualitative test. The colour of the obtained precipitate gives an idea about the quantity of sugar present in the solution. A greenish precipitate indicates about 0.5% concentration; yellow precipitate indicates 1% concentration; orange indicates 1.5% and red indicates 2% or higher concentration. A positive result in the Benedict's test can be recognised for a compound by a 5% (weight/weight) solution of compound in water as a red colouring. The aldehyde group of the sugar allows the sugar to act as a reducing agent, for example in the Benedict's test.

In at least one embodiment, the reducing sugar is selected from the group consisting of: ribose, arabinose, xylose, lyxose, galactose, mannose, and mixtures thereof. In at least one embodiment, the reducing sugar is either ribose, arabinose, or a mixture thereof. In at least one embodiment, the fixing composition comprises a reducing sugar and wherein the reducing sugar is selected from the group consisting of: arabinose, ribose, and mixtures thereof. In at least one embodiment, the sole reducing sugar is a pentose. In at least one embodiment, the sole reducing sugar is selected from the group consisting of: arabinose, ribose, and mixtures thereof. The reducing sugars arabinose, ribose, and mixtures thereof have the benefit of excellent straightening performance By treating hair with reducing sugar and subsequent heat treatment as per the invention the treated hair becomes durably straight. Arabinose and ribose are 5 carbon sugars and these are found to have even better performance than sugars with other carbon numbers, such as 6 carbon and 7 carbon sugars. On the other hand, 6 carbon sugars are highly available and thus have economic advantages. In at least one embodiment, the fixing composition comprises a total amount of reducing sugar being from about 12% to about 18% reducing sugar, and wherein the fixing composition comprises arabinose.

In at least one embodiment, the crosslinking agent comprises a functional group selected from the group consisting of: —C(═O)—, —C(═O)—H, and —C(═O)—O—. In at least one embodiment, the crosslinking agent comprises at least two functional groups functional group selected from the group consisting of: —C(═O)—, —C(═O)—H, —OH, —NH$_2$, and —C(═O)—O—. In at least one embodiment, the crosslinking agent comprises at least two functional groups functional group selected from the group consisting of: —C(═O)—H, —OH, —NH$_2$. In at least one embodiment, the crosslinking agent is a carbonyl compound. In at least one embodiment, the crosslinking agent is an aldehyde. Aldehydes are useful in that they react with amino groups in keratin fibres. Since keratin fibres are polypeptides, available amino groups are common. In another embodiment, the crosslinking agent is 1,2-bis(2maleimidoethoxy)ethane (CAS#115587-84-7).

In at least one embodiment, the crosslinking agent conforms to the formula H$_2$N—(CH$_2$)n-C(═O)—H, wherein n is an integer from 2 to 10, or from 5 to 8, and isomers thereof. In at least one embodiment, the crosslinking agent conforms to the formula H$_3$C—C(═O)—(CH$_2$)n-C(═O)—CH$_3$, wherein n is an integer from 0 to 10, from 1 to 8, or from 2 to 7, and isomers thereof. In at least one embodiment, the crosslinking agent comprises a heterocyclic 5-member ring. In at least one embodiment, the crosslinking agent comprises a heterocyclic 5-member ring comprising nitrogen and oxygen atoms. In at least one embodiment, the crosslinking agent is a ketone. In at least one embodiment, the crosslinking agent is a dial, or a dial having an OH group. In at least one embodiment, the crosslinking agent is an oxazolidone. In at least one embodiment, the crosslinking agent is selected from the group consisting of: 3-(2-hydroxyethyl)-2-oxazolidinone, hexane-2,5-dione, butane-2,3-dione, ethanedial, 2-hydroxy-butanedial, 4-oxo-pentanoic acid, isomers thereof, derivatives thereof, and mixtures thereof. In at least one embodiment, the crosslinking agent is selected from the group consisting of: 3-(2-hydroxyethyl)-2-oxazolidinone, hexane-2,5-dione, butane-2,3-dione, ethanedial, 2-hydroxy-butanedial, 4-oxo-pentanoic acid, and mixtures thereof. In at least one embodiment, the crosslinking agent is selected from the group consisting of: 3-(2-hydroxyethyl)-2-oxazolidinone, hexane-2,5-dione, butane-2,3-dione, 2-hydroxy-butanedial, and mixtures thereof. In at least one embodiment, the crosslinking agent is selected from the group consisting of: butane-2,3-dione; 2-hydroxy-butanedial; 2-hydroxy-butanedial; and mixtures thereof. In at least one embodiment, the crosslinking agent is selected from the group consisting of: butane-2,3-dione; 2-hydroxy-butanedial; 2,3,4-trihydroxy-pentandial; and mixtures thereof.

In at least one embodiment, the crosslinking agent comprises at least two functional groups selected from: —C(OH)— and —C(═O)OH. In at least one embodiment, the crosslinking agent is selected from the group consisting of: 1,2,4-butanetriol, oxobutanedioic acid, butanedioic acid, heptanedioic acid, 1,4-butanediol, 1,6-hexanediol, 1,2,6-hexanetriol, 6-amino-1-hexanol, 6-aminohexanoic acid, 2-aminobutanoic acid, ethane-1,2-diol, aminoethanoic acid, 2-hydroxyethanoic acid, 4-oxopentanoic acid, ethanedioic acid, aminooxoethanoic acid, and mixtures thereof. In at least one embodiment, the crosslinking agent is a diol conforming to the formula HO—(CH$_2$)n-OH, wherein n is an integer from 2 to 12, or isomers thereof. In at least one embodiment, the crosslinking agent is a triol.

In at least one embodiment, the crosslinking agent comprises a —C(═O)OH functional group. Said carboxylic acid group has the advantage that the reaction with OH groups the kertain polypeptide is a more efficient reaction than other chemistries. In at least one embodiment, the crosslinking agent comprises a hydroxyl functional group. The hydroxyl group has the advantage that the crosslinking agent can further provide conditioning to the keratin fibres. In at least one embodiment, the crosslinking agent comprises both a —C(OH)— and a —C(=O)OH functional group. In at least one embodiment, the crosslinking agent conforms to the formula HO—(CH₂)n-COOH, wherein n is an integer from 2 to 12, or from 4 to 10, or from 5 to 8, or isomers thereof. In at least one embodiment, the crosslinking agent conforms to the formula HOOC—(CH₂)n-COOH, wherein n is an integer from 2 to 12, or from 4 to 10, or from 5 to 8, or isomers thereof. In at least one embodiment, the crosslinking agent is selected from the group consisting of: 1,4-butanediol, 1,6-hexanediol, 1,2,4-butanetriol, 1,2,6-hexanetriol, butanedioic acid, heptanedioic acid, and mixtures thereof. In at least one embodiment, the crosslinking agent further comprises a functional group selected from the group consisting of: —NH₂ and —C(=O)—. In at least one embodiment, the crosslinking agent is a triol and has 4 or more carbon atoms. In at least one embodiment, the fixing composition is substantially free of 2-hydroxypropane-1,2,3-tricarboxylic acid and propane-1,2,3-triol.

In at least one embodiment, the crosslinking agent is selected from the group consisting of: 1,4-butanediol, 1,6-hexanediol, 1,2,4-butanetriol, 1,2,6-hexanetriol, butanedioic acid, heptanedioic acid, 2-oxo-butanedioic acid, 6-amino-1-hexanol, 6-amino hexanoic acid, 2-aminobutanoic acid, 1,2-ethanediol, 2-aminoacetic acid, 2-hydroxy-acetic acid, 4-oxo-pentanoic acid, ethanedioic acid, 2-amino-2-oxo-acetic acid, and mixtures thereof. In at least one embodiment, the crosslinking agent is selected from the group consisting of: 1,2,4-butanetriol; oxobutanedioic acid; butanedioic acid; heptanedioic acid; 1,4-butanediol; 1,6-hexanediol; 1,2,6-hexanetriol; and mixtures thereof.

In at least one embodiment, the crosslinking agent is selected from the group consisting of: oxoethanoic acid, 2,2-dihydroxyethanoic acid, 2,2'-oxybis(2-hydroxy)-ethanoic acid, a derivative thereof, and mixtures thereof. In at least one embodiment, the crosslinking agent is 2,2-dihydroxyethanoic acid. In at least one embodiment, the active is a derivative of oxoethanoic acid, 2,2-dihydroxyethanoic acid, or 2,2'-oxybis(2-hydroxy)-ethanoic acid. Suitable derivatives are disclosed in WO2013/117771A1, which is incorporated herein by reference. In at least one embodiment, the active is a salt of oxoethanoic acid, 2,2-dihydroxyethanoic acid, 2,2'-oxybis(2-hydroxy)-ethanoic acid, or a mixture of two or more of said salts. In at least one embodiment, the derivative is selected from the group consisting of: methyl glyoxylate, ethyl glyoxylate, 2-hydroxyethyl glyoxylate, 3-hydroxypropyl glyoxylate, glyceryl glyoxylate, dihydroxyacetone glyoxylate, glyceryl diglyoxylate or triglyoxylate, sorbitol mono-, di- or triglyoxylate, glucose mono-, di- or triglyoxylate, 1,3-propanediol glyoxylate, 1,2-ethanediol glyoxylate, and mixtures thereof. In at least one embodiment, the derivative is selected from the group consisting of formulae 1 to 4 below, and mixtures thereof:

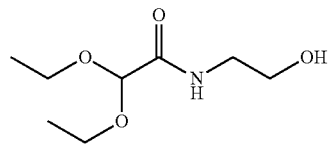

(1)

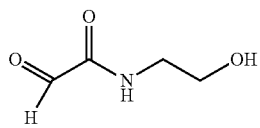

(2)

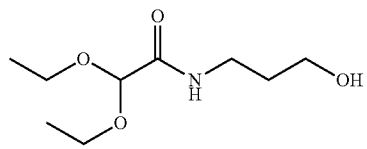

(3)

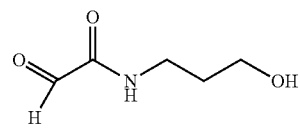

(4)

In at least one embodiment, the derivative is selected from the group consisting of formulae 1' to 6' below, and mixtures thereof:

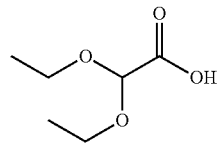

(1')

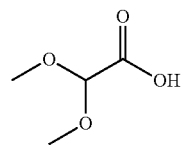

(2')

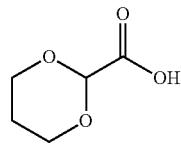

(3')

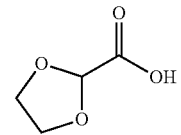

(4')

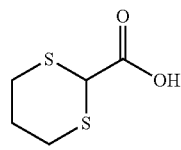

(5')

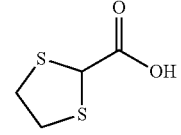

(6')

In at least one embodiment, the derivative is selected from the group consisting of formulae 1" to 5" below, and mixtures thereof:

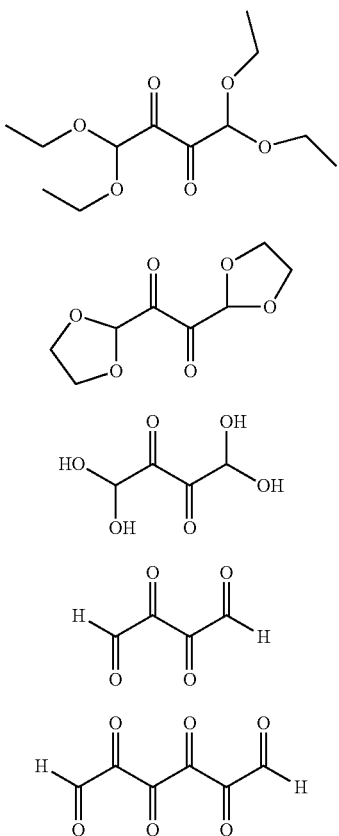

In at least one embodiment, the crosslinking agent is selected from the group consisting of: oxoethanoic acid, 2,2-dihydroxyethanoic acid, 2,2'-oxybis(2-hydroxy)-ethanoic acid, and mixtures thereof. In at least one embodiment, the crosslinking agent is a mixture of oxoethanoic acid, 2,2-dihydroxyethanoic acid, and 2,2'-oxybis(2-hydroxy)-ethanoic acid. In at least one embodiment, the crosslinking agent is 2,2-dihydroxyethanoic acid. Oxoethanoic acid and 2,2-dihydroxyethanoic acid are available from Sigma Aldrich.

In at least one embodiment, the crosslinking agent is selected from the group consisting of: 2-hydroxypropane-1,2,3-tricarboxylic acid, 1,2,3,4-butanetetracarboxylic acid, a derivative thereof, and mixtures thereof. In at least one embodiment, the crosslinking agent is 2-hydroxypropane-1,2,3-tricarboxylic acid. In at least one embodiment, the crosslinking agent is 1,2,3,4-butanetetracarboxylic acid. 2-hydroxypropane-1,2,3-tricarboxylic acid and 1,2,3,4-butanetetracarboxylic acid are available from Sigma Aldrich.

In at least one embodiment, the crosslinking agent is a carbonate ester. In at least one embodiment, the carbonate ester conforms to the formula $R_1O(C=O)OR_2$ wherein $R_1$ and $R_2$ are independently a $C_{1-18}$ alkyl, alkylene, or phenyl, which includes cyclic, non-cyclic, branched chain and straight chain. In at least one embodiment, the carbonate ester conforms to the formula $R_1O(C=O)OR_2$ wherein $R_1$ and $R_2$ are independently a $C_{1-10}$ alkyl or alkylene. In at least one embodiment, the carbonate ester conforms to the formula $R_1O(C=O)OR_2$ wherein $R_1$ and $R_2$ are independently selected from: methyl, ethyl, and phenyl. In at least one embodiment, the carbonate ester is selected from the group consisting of: 1,3-dioxolan-2-one; dimethyl carbonate; diethyl carbonate; diphenyl carbonate; 1,3-dioxan-2-one (trimethylene carbonate); 4-methyl-1,3-dioxolan-2-one; and mixtures thereof.

In another embodiment, the crosslinking composition comprises a second crosslinking agent. Without wishing to be bound by theory, the second crosslinking agent is useful for reacting with and providing further crosslinks in keratin. The hair comprises polypeptides of keratin having functional groups —COOH, OH, and $NH_2$, and SH. Different active agents can react preferentially with each functional group. For instance, arabinose preferentially reacts with amino groups whereas ethylene carbonate reacts preferentially with —COOH.

The second crosslinking agent may be liquid at 25° C. Second crosslinking agents being liquid at this temperature have the advantage of providing improved hair feel versus second crosslinking agents that are solid at this temperature.

In one embodiment first and second crosslinking agents are present in the crosslinking composition at a weight ratio of about 2:1 arabinose:ethylene carbonate or about 1:3 arabinose:ethylene carbonate or about 1:6 arabinose:ethylene carbonate, or about 1:12 to about 3:12 arabinose:ethylene carbonate, or about 7:4 to about 9:4 arabinose:ethylene carbonate, or about 2:9 to about 4:9 arabinose:ethylene carbonate. The crosslinking composition may comprise from about 0.1% to about 40%, or from about 0.5% to about 20%, or from about 1% to about 15%, or from about 7% to about 20%, or from about 8% to about 19%, or from about 10% to about 18% arabinose:ethylene carbonate at the about 2:1, about 1:6, or about 1:3 weight ratio.

In at least one embodiment, the crosslinking composition comprises from about 7% to about 20%, or from about 8% to about 19%, or from about 10% to about 18% arabinose:ethylene carbonate. In at least one embodiment, the crosslinking composition comprises from about 12% to about 18% arabinose:ethylene carbonate at a weight ratio of about 2:1, about 1:6, or about 1:3.

In at least one embodiment, the crosslinking composition may have a pH of from about pH 2 to about pH 11. In at least one embodiment, the crosslinking composition has a pH of from about pH 3.5 to about pH 10.75, or from about pH 4.0 to about pH 10.5, or from about pH 4.5 to about pH 10.25, or from about pH 4.0 to about pH 10.0, or from about pH 3.5 to about pH 9.5, or from about pH 3.5 to about pH 9.0, or from about pH 3.0 to about pH 8.5. A basic pH may be useful for crosslinking agents in view of penetration into hair. In at least one embodiment, the crosslinking composition comprises a buffering agent. In at least one embodiment, the buffering agent is a phosphate buffer. In at least one embodiment, the buffering agent is a borate buffer or a carbonate buffer. In at least one embodiment, the buffering agent is selected from the group consisting of: glycine/sodium hydroxide; sodium carbonate/sodium hydrogen carbonate, sodium tetraborate/sodium hydroxide; sodium bicarbonate/sodium hydroxide; ammonium chloride/ammonia. The buffering agent has the advantage of controlling the pH, which aids the stability of the crosslinking composition. In at least one embodiment, the crosslinking composition comprises an alkalizing agent and/or an agent for adjusting the pH value. The crosslinking composition may further comprise a protonating agent. The protonating agent may be a monoprotic or polyprotic acid, water-soluble or water-insoluble acid, and/or an organic or inorganic acid. In at least one embodiment, the protonating agent is selected from formic acid, acetic acid, sulfuric acid, hydrochloric acid, citric acid, and mixtures thereof. In at least one embodiment, the protonating agent is citric acid. Citric acid is useful because it is naturally available from lemons.

In at least one embodiment, the crosslinking composition further comprises one or more cosmetic agents, including but not limited to: buffering agents, conditioning agents, emulsifying agents, cosmetically acceptable carriers, antioxidants, chelating agents, surfactants, hair styling polymers, and preservatives.

In at least one embodiment, the crosslinking composition may comprise one or more photocatalysts. These catalysts can be particularly useful when using a device capable of emitting radiation with a wavelength from about 300 nm to about 750 nm. In at least one embodiment, the crosslinking composition has not been exposed to electromagnetic radiation prior to applying to the keratin fibers. In at least one embodiment, the crosslinking composition is store in an opague container prior to use. In at least one embodiment, the crosslinking composition is stored in an amber vial prior to use.

Photocatalysts

In at least one embodiment, the crosslinking composition may comprise a photocatalyst comprising a hydroxy-substituted aromatic compound. Photocatalysts may be utilized when using a device capable of emitting radiation with a wavelength of about 300 nm to about 750 nm. A photocatalyst is an acid or base (or conjugate thereof) having a pKa (or pKb) value that decreases (or increases) upon exposure to electromagnetic radiation, particularly light. Photoacids are mentioned for example in Domcke and Sobolewski (2003), Unraveling the Molecular Mechanisms of Photoacidity, 302, p. 1693 and in Kowalewska (2005), *Photoacid catalyzed sol-gel process*, J. Mater. Chem. 15, p. 4997, which are both incorporated herein by reference. In at least one embodiment, the electromagnetic radiation is selected from the group consisting of: ambient light, sunlight, incandescent light, fluorescent light, LED light, laser light, and combinations thereof. In at least one embodiment, the electromagnetic radiation is selected from the group consisting of: visible light, near or far ultraviolet light, or near or far infrared light, and combinations thereof. In at least one embodiment, the photocatalyst can be activated to a photo-excited state by excitation with incident radiation with a wavelength from about 300 nm to about 750 nm and wherein the appliance emits radiation with a wavelength from about 300 nm to about 750 nm.

In at least one embodiment, the hydroxy-substituted aromatic compound is a quinoline compound or a naphthol compound. In at least one embodiment, the hydroxy-substituted aromatic compound is a fluorescein or a derivative thereof. In at least one embodiment, the hydroxy-substituted aromatic compound is a halogen-substituted fluorescein. In at least one embodiment, the hydroxy-substituted aromatic compound is bromo- or iodo-substituted fluorescein. In at least one embodiment, the hydroxy-substituted aromatic compound is selected from the group consisting of: diiodofluorescein, 4,5,6,7-tetrachloro-2',4',5',7'-tetraiodofluorescein (rose Bengal), a salt of 2,4,5,7-tetraiodofluorescein (erythrosine), Eosin Y, Eosin B, 4,5-dibromofluorescein, and mixtures thereof. In at least one embodiment, the hydroxy-substituted aromatic compound is a hydroxyflavone or a derivatives thereof. In at least one embodiment, the hydroxy-substituted aromatic compound is a dihydroxyflavone or a trihydroxyflavone or a tetrahydroxyflavone or a mixture thereof. In at least one embodiment, the hydroxy-substituted aromatic compound is selected from the group consisting of: 3-hydroxy flavones, 7-hydroxy flavones, 5,7-hydroxy flavones, 4,5,7-trihydroxyflavone, 2-(3,4-dihydroxyphenyl)-3,5,7-trihydroxy-4H-chromen-4-one (quercitin), and mixtures thereof. In at least one embodiment, the hydroxy-substituted aromatic compound is a hydroxyltriarylmethane, for example FD&C Green 3. In at least one embodiment, the hydroxy-substituted aromatic compound is an anthocyanidins or an anthocyanin. In at least one embodiment, the hydroxy-substituted aromatic compound is cyanidin (2-(3,4-dihydroxyphenyl) chromenylium-3,5,7-triol), malvidin, palargonidin or extracts containing anthocyanins such as elderberry, blueberry, cranberry, bilberry, red cabbage, sorghums, blackberry, black current, cherry red and black raspberry, and mixtures thereof.

In at least one embodiment, the hydroxy-substituted aromatic compound is selected from the group consisting of: 8-hydroxyquinoline, 8-hydroxyquinoline sulfate, 8-quinolinol-1-oxide, 5-hydroxyquinoline, 6-hydroxyquinoline, 7-hydroxyquinoline, 5-iodo-7-sulfo-8-hydroxyquinoline, 5-fluoro-8-hydroxyquinoline, 5-fluoro-7-chloro-8-hydroxyquinoline, 5-fluoro-7-bromo-8-hydroxyquinoline, 5-fluoro-7-iodo-8-hydroxyquinoline, 7-fluoro-8-hydroxyquinoline, 5-chloro-8-hydroxyquinoline, 5,7-dichloro-8-hydroxyquinoline, 5-chloro-7-brono-8-hydroxyquinoline, 5-chloro-7-iodo-8-hydroxyquinoline, 7-chloro-8-hydroxyquinoline, 5-bromo-8-hydroxyquinoline, 5-bromo-7-chloro-8-hydroxyquinoline, 5,7-dibromo-8-hydroxyquinoline, 5-bromo-7-iodo-8-hydroxyquinoline, 7-bromo-8-hydroxyquinoline, 5-iodo-8-hydroxyquinoline, 5-iodo-7-chloro-8-hydroxyquinoline, 5,7-diiodo-8-hydroxyquinoline, 7-iodo-8-hydroxyquinoline, 5-sulfonic acid-8-hydroxyquinoline, 7-sulfonic acid-8-hydroxyquinoline, 5-sulfonic acid-7-iodo-8-hydroxyquinoline, 5-thiocyano-8-hydroxyquinoline, 5-chloro-8-hydroxyquinoline, 5-bromo-8-hydroxyquinoline, 5,7-dibromo-8-hydroxyquinoline, 5-iodo-8-hydroxyquinoline, 5,7-diiodo-8-hydroxyquinoline, 7-azaindole, 7-cyano-2-naphthol, 8-cyano-2-naphthol, 5-cyano-2-naphthol, 1-hydroxy-3,6,8-pyrenetrisulfonic acid, Trans-3-hydroxystilbene, 2-hydroxymethylphenol, Pelargonidin, and mixtures thereof. In at least one embodiment, the hydroxy-substituted aromatic compound is selected from the group consisting of: 8-quinolinol-1-oxide, 8-hydroxyquinoline, 7-cyano-2-naphthol, 8-cyano-2-naphthol, 5-cyano-2-naphthol, and mixtures thereof. In at least one embodiment, the hydroxy-substituted aromatic compound is selected from the group consisting of: 8-quinolinol-1-oxide, 8-hydroxyquinoline, and mixtures thereof. In at least one embodiment, the hydroxy-substituted aromatic compound is 8-hydroxyquinoline. 8-hydroxyquinoline may act as a photoacid catalyst in lower pH solutions or as a photobase catalyst in higher pH solutions. 8-hydroxyquinoline has the CAS Number 148-24-3 and is available from Sigma-Aldrich. In at least one embodiment, the hydroxy-substituted aromatic compound is multi-cyclic. 8-hydroxyquinoline has the advantage of being easily available and characterised for use in cosmetic compositions such as hair dye compositions.

In at least one embodiment, the crosslinking composition comprises from about 10 ppm to about 500 ppm photocatalyst being a hydroxy-substituted aromatic compound. The concentration of photocatalyst may dependent, in part, on a variety of factors including, for example, the chemical structure of the photocatalyst, the reaction medium, the reaction type, and the substrate. In at least one embodiment, the crosslinking composition comprises from about 20 ppm to about 500 ppm, or from about 30 ppm to about 450 ppm, or from about 30 ppm to about 400 ppm, or from about 50 ppm to about 350 ppm, or from about 70 ppm to about 330 ppm, or from about 80 ppm to about 310 ppm, or from about 90 ppm to about 300 ppm, or from about 100 ppm to about 290 ppm, or to about 260 ppm, or to about 250 ppm, or to about 240 ppm, or to about 220 ppm, or to about 210 ppm, or to about 200 ppm photocatalyst being a hydroxy-substituted aromatic compound. To note: 1 ppm=1 parts per million=$1\times10^{-4}\%$=0.0001% and 10 ppm=$1\times10^{-3}\%$=0.001% and 100 ppm=$1\times10^{-2}\%$=0.01%.

When the crosslinking composition comprises a photocatalyst, the crosslinking composition may not have been exposed to electromagnetic radiation having a wavelength of 750 nm or less and for 30 min or more. The exposure of the crosslinking composition is important in view of the efficacy of the photocatalyst since when it is exposed to electromagnetic radiation within a certain wavelength range it will react with surround molecules if they are available, including compounds in the packaging wall. In at least one embodiment, the crosslinking composition is packaged in a container where electromagnetic radiation having a wavelength of 750 nm or less is not able to contact the crosslinking composition. In at least one embodiment, the crosslinking composition has not been exposed to electromagnetic radiation having a wavelength of 750 nm or less, or from about 300 nm to about 750 nm, or visible light, or UV light, and for 20 min or more, or 10 min or more, or 2 min or more. In at least one embodiment, the crosslinking composition is packaged in an opaque container. In at least one embodiment, the crosslinking composition is packaged in an amber- or brown-coloured container.

Cosmetic Agents

In at least one embodiment, the pretreatment and/or the crosslinking composition may comprise one or more cosmetic agents. Cosmetic agents are useful in providing cosmetic benefits to the keratin fibers and formulating more stable pretreatment and/or crosslinking compositions. The pretreatment composition may comprise the same or different cosmetic agents as the crosslinking composition.

In at least one embodiment, the cosmetic agent may be a cosmetically acceptable carrier. In at least one embodiment, the cosmetically acceptable carrier is any carrier suitable for formulating the active agent into a crosslinking and/or pretreatment composition being suitable for application onto hair. In at least one embodiment, the cosmetically acceptable carrier is selected from either an aqueous medium or an aqueous-alcoholic medium. In at least one embodiment, when the carrier is an aqueous-alcoholic carrier, this carrier comprises water and an alcohol. In at least one embodiment, the alcohol is selected from the group consisting of: ethanol, isopropanol, propanol, and mixtures thereof. In at least one embodiment, when the carrier is an aqueous carrier, this carrier consists essentially of water and is substantially free of alcohol. In at least one embodiment, the crosslinking and/or pretreatment composition comprises a safe and effective amount of cosmetically acceptable carrier. In at least one embodiment, the carrier is present from about 0.1% to about 99%, or from about 1% to about 98%, or from about 10% to about 97%, or from about 30% to about 95% water.

In at least one embodiment, the cosmetic agent may be an antioxidant. Antioxidants are useful in view of providing longer-term stability for the crosslinking and/or pretreatment composition. In at least one embodiment, the crosslinking and/or pretreatment composition comprises a safe and effective amount of an antioxidant. In at least one embodiment, the antioxidant is present from about 0.001% to about 5%, or from about 0.5% to about 1.0% antioxidant. In at least one embodiment, the antioxidant is selected from the group consisting of: ascorbic acid (vitamin C), ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, peroxides including hydrogen peroxide, perborate, thioglycolates, persulfate salts, 6-hydroxy-2,5,7,8-tetramethylchroman-2-carboxylic acid (commercially available under the tradename Trolox™), gallic acid and its alkyl esters, especially propyl gallate, uric acid and its salts and alkyl esters, ferulic acid and its salts and esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, 1-methionine, proline, superoxide dismutase, silymarin, tea extracts, grape skin and/or grape seed extracts, melanin, rosemary extracts, and mixtures thereof. In at least one embodiment, the antioxidant is tocopherol sorbate or an ester of tocopherol. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee. In at least one embodiment, the antioxidant is sodium benzoate. In at least one embodiment, the antioxidant is ferulic acid. Ferulic acid has the benefit of enhancing the oxidative stability of the formulation. In at least one embodiment, the crosslinking and/or pretreatment composition comprises a safe and effective amount of ferulic acid. In at least one embodiment, the antioxidant comprises from about 0.001% to about 5%, or from about 0.5% to about 1.0% ferulic acid.

In at least one embodiment, the cosmetic agent may be a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage, in order to decrease the local iron load, which generates, as indicated above, a pro-oxidant situation and pigmentation. A chelating agent is useful in view of providing longer-term stability for the crosslinking composition. In at least one embodiment, the pretreatment and/or crosslinking composition comprises a safe and effective amount of a chelator or chelating agent. In at least one embodiment, the pretreatment and/or crosslinking composition comprises a chelating agent, and wherein the chelating agent is selected from the group consisting of: N-hydroxysuccinimide, EDTA, NTA, deferoxamine, hydroxamic acids and their salts, phytic acid, phytate, gluconic acid and its salts, transferrine, lactoferrin, and mixtures thereof. In at least one embodiment, the crosslinking and/or preatreatment composition comprises a safe and effective amount of chelating agent. In at least one embodiment, the chelating agent may be present from about 0.001% to about 10%, or from about 0.01% to about 5%, or from about 0.1% to about 5%, or from about 0.5% to about 1.0% chelating agent. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. In at least one embodiment, the chelating agent is selected from the group consisting of: N-hydroxysuccinimide deferoxamine, lactoferrin, hydroxamic acids, gluconic acid, phytic acid, derivatives thereof, and mixtures thereof.

In at least one embodiment, the preatreatment and/or crosslinking composition is in a form suitable for application onto hair. In at least one embodiment, the preatreatment and/or crosslinking composition may be in the form of an emulsion, a solution, or a dispersion. In at least one embodiment, the preatreatment and/or crosslinking composition comprises a cosmetic agent which may be a surfactant. The surfactant can be useful in providing an emulsion. In at least one embodiment, when being in the form of an emulsion, said emulsion may be a water-in-oil emulsion, an oil-in-water emulsion, or a multiple emulsion. An emulsion has the benefit of providing an easy-to-apply composition for the consumer to apply to the hair and has aesthetic advantages. The crosslinking and/or pretreatment composition may be a leave-in composition or a rinse-off composition. The crosslinking and/or pretreatment composition may be in a form selected from: a shampoo; a hair conditioning composition; a hairstyling composition; or combinations thereof. When being a hairstyling composition, said composition may be a gel composition; a spray gel composition, optionally dispensed using a mechanical spray device and/or at least one propellant; a non-aerosol hairspray, optionally dispensed using a suitable mechanically operated spraying device; a foamable composition, optionally dispensed using devices for foaming; hair wax composition; hair lotion composition; hair cream composition; or combinations thereof. In at least one embodiment, the crosslinking and/or pretreatment composition is a mascara composition.

In at least one embodiment, the cosmetic agent may be a hair styling polymer selected from the group consisting of: non-ionic hairstyling polymer, anionic hairstyling polymer, zwitterionic and/or amphoretic hairstyling polymer, cationic hair styling polymer, or mixtures thereof. Suitable hairstyling polymers may be found in the CTFA International Cosmetics Ingredient Dictionary and Handbook, "Hair Fixatives", 12$^{th}$ edition (2008). Suitable hairstyling polymers are, for example, those materials disclosed from page 12, line 5 to page 19, line 1 of the European patent application 08151246.9 filed on 11 Feb. 2008, which is incorporated herein by reference.

In at least one embodiment, the crosslinking and/or pretreatment composition comprises from about 0.01% to about 10% by weight, or from about 0.1% to about 8%, or from about 0.1% to about 5% hairstyling polymer.

In at least one embodiment, the cosmetic agent may be a non-ionic hairstyling polymer. In at least one embodiment, the non-ionic hairstyling polymer is a natural or synthetic polymer. In at least one embodiment, the non-ionic hair styling polymers is a polymer obtained from the polymerisation of at least one type of monomer selected from: vinylpyrrolidone; vinylcaprolactam; vinyl esters; vinyl alcohol; vinyl acetate; (meth)acrylamide, and/or its derivatives; (meth)acrylic acid, its salts, and/or its derivatives; propylene and/or ethylene glycol acid; crotonic acid; or mixtures thereof. For example, such polymers are available under the trade names Luviskol® or Luviset Clear®.

In at least one embodiment, the cosmetic agent may be an anionic hairstyling polymer. In at least one embodiment, the anionic hairstyling polymer is selected from the group consisting of: acrylic acid/alkyl acrylate/Nalkylacrylamide terpolymer; vinyl acetate/crotonic acid copolymer; C1-C5-alkyl acrylate/(meth)acrylic acid copolymer; sodium polystyrenesulfonate; vinyl acetate/crotonic acid/vinyl alkanoate copolymer; vinyl acetate/crotonic acid/vinyl neodecanoate copolymer; aminomethylpropanol acrylate copolymer; vinylpyrrolidone/(meth)acrylic copolymer; methyl vinyl ether/maleic monoalkyl esters copolymer; aminomethylpropanol salts of allyl methacrylate/(meth)acrylate copolymer; ethyl acrylate/methacrylic acid copolymer; vinyl acetate/mono-nbutyl maleate/isobornyl acrylate copolymer; octylacrylamid/(meth)acrylic acid copolymer; polyesters of diglycol, cyclohexanedimethanol, isophthalic acid and sulfoisophthalic acid; and mixtures thereof.

In at least one embodiment, the cosmetic agent may be a zwitterionic or amphoteric hairstyling polymer. In at least one embodiment, the zwitterionic or amphoteric hairstyling polymer is selected from the group consisting of: alkylacrylamide/alkylaminoalkyl methacrylate/(meth)acrylic acid copolymers; copolymers which are formed from at least one first monomer type which has quaternary amine groups, and at least one second monomer type which has acid groups; copolymers of fatty alcohol acrylates, of alkylamine oxide methacrylate and at least one monomer chosen from acrylic acid and methacrylic acid; methacryloylethylbetaine/methacrylic acid and/or esters copolymers; polyquaternium-47; polyquaternium-43; oligomers or polymers, preparable from quaternary croton betaines or quaternary croton betaine esters; or mixtures thereof.

In at least one embodiment, the cosmetic agent may be a cationic hairstyling polymer. In at least one embodiment, the cationic hairstyling polymer is selected from the group consisting of homopolymers or copolymers where a quaternary nitrogen groups are present either in the polymer chain or as substituent on one or more of the cationic monomers. The monomers containing ammonium groups may be copolymerized with non-cationic monomers. Suitable cationic monomers may be unsaturated, free-radically polymerizable compounds which carry at least one cationic group, in particular ammonium-substituted vinyl monomers, such as, for example, trialkylmethacryloxyalkylammonium, trialkylacryloxyalkyl ammonium, dialkyldiallylammonium and quaternary vinylammonium monomers with cyclic, cationic nitrogen-containing groups, such as pyridinium, imidazolium or quaternary pyrrolidones, e.g. alkylvinylimidazolium, alkylvinylpyridinium, or alkylvinylpyrrolidone salts. The alkyl groups of these monomers are preferably lower alkyl groups, such as, for example, C1 to C7-alkyl groups, particularly preferably C1 to C3-alkyl groups. Suitable non-cationic monomers may be selected from (meth)acrylamide, derivatives thereof; acrylate, its derivative thereof; vinylcaprolactone, vinylcaprolactam, vinylpyrrolidone, vinyl esters, vinyl alcohol, propylene glycol or ethylene glycol. For example, suitable cationic hairstyling polymers are available under the tradenames Gafquat 755 N; Gafquat 734; Gafquat HS 100; Luviquat HM 550; Merquat Plus 3300; Gaffix VC 713; Aquaflex SF 40. In at least one embodiment, the crosslinking composition comprises a cationic hairstyling polymer derived from a natural polymer. In at least one embodiment, the cationic hairstyling polymer derived from a natural polymer is derived from a natural polymer selected from the group consisting of: cationic derivatives polysaccharides such as cellulose, starch and/or guar; chitosan, its salts, and/or its derivatives; or mixtures thereof. In at least one embodiment, the cationic hairstyling polymers are selected from the group consisting of: polyquaternium-4; polyquatemium-10; polyquaternium-24; guar hydroxypropyltrimonium chloride; chitosonium pyrrolidonecarboxylate; and mixtures thereof.

In at least one embodiment, the cosmetic agent may be a conditioning agent, or a hair conditioning agent. The cosmetic agent may be any suitable and conventional hair conditioning agents. The term "hair conditioning agent" herein means any cosmetically acceptable compound having a cosmetic effect on hair, such as providing gloss to hair, making hair more manageable, improving hair touch, improving combability and/or giving hair more volume. Suitable hair conditioning agents may be found in the CTFA International Cosmetics Ingredient Dictionary and Handbook, "Hair conditioning agents", 12$^{th}$ edition (2008). In at least one embodiment, the hair conditioning agent is selected from the group consisting of: cationic surfactants, non-ionic surfactants, silicone compounds, organic oily conditioning agents, and mixtures thereof. Suitable hair conditioning agents are, for example, those materials disclosed from page 19, line 3 to page 27, line 33 of the European patent application 08151246.9 filed on 11 Feb. 2008, which is incorporated herein by reference.

In at least one embodiment, the conditioning agent is a cationic surfactant. In at least one embodiment, the cationic surfactant comprises amino or quaternary ammonium moieties. In at least one embodiment, the crosslinking and/or pretreatment composition comprises from about 0.05% to about 3.5%, or from about 0.1% to about 3.0%, or from about 0.5% to about 2.5%, or from about 1.0% to about 2.0% cationic surfactant. In at least one embodiment, cationic surfactant is according to Formula II:

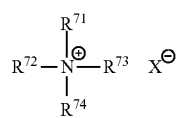

wherein at least one of $R^{71}$, $R^{72}$, $R^{73}$ and $R^{74}$ is selected from: an aliphatic group of from 8 to 30 carbon atoms; an aromatic, alkoxy, polyoxyalkylene, alkylamido, hydroxyalkyl, aryl; or an alkylaryl group having from 7 to 22 carbon atoms; wherein the remainder of $R^{71}$, $R^{72}$, $R^{73}$ and $R^{74}$ are independently selected from the group consisting of: an aliphatic group consisting of from 1 to 22 carbon atoms; and an aromatic, alkoxy, polyoxyalkylene, alkylamido, hydroxyalkyl, aryl or alkylaryl group having up to 22 carbon atoms; wherein X is selected from the group consisting of: halogen, acetate, citrate, lactate, glycolate, phosphate, nitrate, sulfonate, sulfate, alkylsulfate, alkyl sulfonate radicals, and mixtures thereof. In at least one embodiment, cationic surfactant is according to Formula II (see above), wherein at least one of $R^{71}$, $R^{72}$, $R^{73}$ and $R^{74}$ is an aliphatic group having from 16 to 24 carbon atoms; wherein the remainder of $R^{71}$, $R^{72}$, $R^{73}$ and $R^{74}$ are independently selected from the group consisting of aliphatic groups having from 1 to 4 carbon atoms; wherein X is selected from the group consisting of: chloride or sulfate. In at least one embodiment, the cationic surfactant is selected from the group consisting of: behenyltrimethylammonium chloride, methyl sulfate or ethyl sulfate; stearyltrimethylammonium chloride, methyl sulfate or ethyl sulfate; and mixtures thereof. It is believed that a longer alkyl group provides improved smoothness and soft feeling on wet and dry hair, compared to cationic surfactants with a shorter alkyl group. It is also believed that such cationic surfactants can provide reduced scalp irritation, compared to those having a shorter alkyl group. In at least one embodiment, the cationic surfactant is a di-long alkyl quaternized ammonium salt selected from the group consisting of: dialkyl (14-18 carbons) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and mixtures thereof. In at least one embodiment, the cationic surfactant is a tertiary amidoamine having an alkyl group of from about 12 to about 22 carbons. In at least one embodiment, the cationic surfactant is selected from the group consisting of: cetyl trimethyl ammonium salts; behenyl trimethyl ammonium salts; dimethyl ditallow ammonium salts; stearyl amidopropyl dimethylamine; (di)esterquats; quaternium 8, 14, 15, 18, 22, 24, 26, 27, 30, 33, 37, 53, 60, 61, 72, 78, 80, 81, 82, 83, 84, and/or 91; or mixtures thereof.

In at least one embodiment, the conditioning agent is a non-ionic surfactant. Suitable non-ionic surfactants may be surfactants having a HLB of less than 8. Suitable nonionic surfactants may be selected from glyceryl esters; sugar esters; alkylpolyglucoside ethers; oleyl- or isostearylpolyglucoside; polyoxyethylene (20) sorbitan monostearate; or mixtures thereof.

In at least one embodiment, the conditioning agent is a silicone compound. In at least one embodiment, the silicone compound is volatile or nonvolatile, and/or soluble or insoluble silicones. For example, suitable silicone conditioning agents are available under the tradenames SF 1075 methyl phenyl fluid (Electric company); DC200 Fluid, DC244, DC245, DC345, Dow 5-7113, DC556 Cosmetic Grade Fluid, DC1248 (Dow Corning). In at least one embodiment, the crosslinking composition comprises a conditioning agent being the reaction product of: (a) an aminosilane; (b); polysiloxane; and optionally (c) a polyether. In at least one embodiment, the crosslinking composition comprises a conditioning agent being the reaction product of: (a) an aminosilane; (b); polysiloxane; and (c) a polyether. In at least one embodiment, the crosslinking composition comprises a conditioning agent, and wherein the conditioning agent is selected from the group consisting of: epoxyaminosilane copolymers, and polysiloxane/polyurea block copolymers, and mixtures thereof. In at least one embodiment, the crosslinking composition comprises a conditioning agent being the reaction product of: (a) an aminosilane; (b) polysiloxane; and (c) a polyether; and optionally (d) an amine. In at least one embodiment, the polysiloxane is an epoxy encapped polysiloxane. In at least one embodiment, the polysiloxane comprises at least two oxirane or oxetane groups. In at least one embodiment, the polysiloxane comprises from about 10 to about 450 silicon atoms, or from about 40 to about 400 silicon atoms, from about 75 to about 350 silicon atoms, from about 150 to about 250 silicon atoms. In at least one embodiment, the polysiloxane is an epoxy encapped polysiloxane. In at least one embodiment, the polyether has the average structure $CH_2(O)CHCH_2O(CH_2(CH_3)CH_2O)_nCH_2CH(O)CH_2$ wherein n is an integer from 1 to 10. In at least one embodiment, the amine comprises from 1 to 10 carbon atoms, or from 2 to 5 carbon atoms. In at least one embodiment, the amine is an alkylamine that is substituted with at least one alkyl group. In at least one embodiment, the amine is selected from the group consisting of: methylamine, ethylamine, propylamine, ethanol amine, isopropylamine, butylamine, isobutylamine, hexylamine, dodecylamine, oleylamine, aniline aminopropyltrimethylsilane, aminopropyltriethylsilane, aminomorpholine, aminopropyldiethylamine benzylamine, napthylamine 3-amino-9-ethylcarbazole, 1-aminoheptaphlorohexane, 2,2,3,3,4,4,5,5,6,6,7,7,8,8,8-pentadecafluoro-1-octanamine, and mixtures thereof. In at least one embodiment, the amine is selected from the group consisting of: methylethylamine, methylhexylamine, methyloctadecylamine, diethanolamine, dibenzylamine, dihexylamine dicyclohexylamine, piperidine, pyrrolidine phthalimide, and mixtures thereof. In at least one embodiment, the conditioning agent is an epoxyaminosilane copolymer. In at least one embodiment, the conditioning agent is conditioning agent being the reaction product of: (a) an aminosilane; (b) polysiloxane, wherein the polysiloxane comprises from about 10 to about 450 silicon atoms, or from about 40 to about 400 silicon atoms; and (c) a polyether; and (d) an amine, wherein the amine is an alkylamine that is substituted with at least one alkyl group. Epoxyaminosilane copolymers are described in EP2214633B1 (filing date 30 Oct. 2008, which is incorporated herein by reference) and are available from Momentive™ Performance Materials Inc., Columbus, Ohio, USA. Epoxyaminosilane copolymers have excellent durability benefits. Such an exemplary expoxyaminosilane copolymer may be synthesised as follows: aminopropyltriisopropoxy silane (40.77 g), an epoxy encapped polysiloxane with the average structure $CH_2(O)CHCH_2OCH_2CH_2Si(CH_3)_2O[Si(CH_3)_2O]_{50}Si(CH_3)_2CH_2CH_2CH_2OCH_2CH(O)CH_2$ (171.40 g) and an epoxy endcapped polyether with the average structure $CH_2(O)CHCH_2O(CH_2(CH_3)CH_2O)_7CH_2CH(O)CH_2$ (37.83 g) and isopropanol (425.68 g) is combined in a 500 mL flask. The material is brought to reflux and stirred with an overhead stirrer. The refluxing continued for 15.5 hr until all epoxy groups are consumed as determined by titration. The material is transferred to a rotary evaporator and stripped at 70° C. and 532 Pa (4 torr) for 2 hrs to remove the isopropanol. Another exemplary expoxyaminosilane copolymer may be synthesised as follows: aminopropyltriisopropoxy silane (14.27 g), 3-(diethylamino)propylamine (7.05 g), an epoxy encapped polysiloxane with the average structure $CH_2(O)CHCH_2OCH_2CH_2CH_2Si(CH_3)_2O[Si(CH_3)_2O]_{200}Si(CH_3)_2CH_2CH_2CH_2OCH_2CH(O)CH_2$ (447.87 g) and an epoxy encapped polyether with the average structure $CH_2(O)CHCH_2O(CH_2CH_2O)_{14}CH_2CH(O)CH_2$ (30.81 g) and isopropanol (500 g) is combined in a 2000 mL flask. The material is brought to reflux and stirred with an overhead stirrer. The refluxing continued for 24 hr until all epoxy groups are consumed as determined by titration. The material is transferred to a rotary evaporator and stripped at 70° C. and 532 Pa (4 torr) for 2 hrs to remove the isopropanol.

In at least one embodiment, the conditioning agent is selected from the group consisting of: epoxyaminosilane copolymers, and polysiloxane/polyurea block copolymers, and mixtures thereof. A polysiloxane/polyurea block copolymer is described in EP2074986B1 filed on 10 Dec. 2008, which is incorporated herein by reference. In at least one embodiment, the polysiloxane/polyurea block copolymer comprises at least one polysiloxane sequence (or block) and at least one polyurea sequence (block) in the backbone of the copolymer. In at least one embodiment, the amount of polysiloxane present in the copolymer is greater than 90% by weight relative to the total weight of the polysiloxane/polyurea block copolymer. In at least one embodiment, the polysiloxane/polyurea block copolymer of the does not comprise polyurethane. By way of non-limiting example, the copolymer can be a non-ionic polysiloxane/polyurea copolymer, that is to say that it does not comprise an ionized or ionizable group. By way of example of a copolymer, non-limiting mention may be made of the dimethylpolysiloxane/polyurea block copolymer having the INCI name polyureadimethicone. Such a dimethylpolysiloxane/polyurea block copolymer can be obtained, for instance, by copolymerization of an α,ω-aminosilicone with a diisocyanate. Polysiloxane/polyurea block copolymers corresponding to these characteristics are, for example, the products sold under the reference Wacker-Belsil® UD 60, Wacker-Belsil® UD 80, Wacker-Belsil® DU 140 and Wacker-Belsil® UD 200 by Wacker. In at least one embodiment, the polysiloxane/polyurea copolymer is non-ionic. In at least one embodiment, the crosslinking composition comprises from about 0.05 to about 20%, for example from 0.1 to 15%, or from 0.5 to 10% polysiloxane/polyurea block copolymer. In at least one embodiment, the conditioning agent is a polydimethylsiloxane-derivative comprising aminoalkyl groups and having an amine number of at least 0.1 meq/g of polydimethylsiloxane. Such polydimethylsiloxane-derivative can, for example, be methoxy-terminated or hydroxy-terminated, or mixtzures thereof. The polydimethylsiloxane-derivative can, for example be a mixture of methoxy- and hydroxy-terminated Poly[3((2-aminoethyl)amino)propyl]methyl(dimethyl)siloxan as commercially sold under Wacker-Belsil® ADM 1370.

In at least one embodiment, the conditioning agent is an organic oily conditioning agent. In at least one embodiment, the organic oily conditioning agent is non-volatile, water-insoluble, oily or fatty. Organic oily conditioning agents may be selected from hydrocarbon oils and fatty esters. In at least one embodiment, the conditioning agent is a fatty alcohol. In at least one embodiment, the fatty alcohol is a non-volatile low melting point fatty alcohol. In at least one embodiment, the conditioning agent is a fatty alcohol and the fatty alcohol is selected from the group consisting of: capryl alcohol, lauryl alcohol, stearyl alcohol, cetyl alcohol, myristyl alcohol, palmitoleyl alcohol, and mixtures thereof.

The crosslinking composition may further comprise at least one direct hair dye. In at least one embodiment, the crosslinking composition may comprise from about 0.01% to about 15%, or from about 0.1% to about 10%, or from about 0.5% to about 8% direct hair dye.

The crosslinking and/or pretreatment composition may further comprise at least one viscosity-modifying agent. In at least one embodiment, the crosslinking composition comprises from about 0.01% to about 20%, or from about 0.05% to about 10%, or from about 0.1% to about 5% viscosity-modifying agent.

The crosslinking and/or pretreatment composition may further comprise at least one emulsifier and/or surfactant. In at least one embodiment, the emulsifier and/or surfactant is selected from nonionic surfactants; anionic surfactants; amphoretic surfactants; or mixtures thereof. In at least one embodiment, the crosslinking and/or pretreatment composition comprises from about 0.01% to about 20%, or from about 0.05% to about 10%, or from about 0.1% to about 5%, emulsifier and/or surfactant.

The crosslinking and/or pretreatment composition may further comprise at least one pigment. In at least one embodiment, the pigment is selected from natural pigments; synthetic pigments; or mixtures thereof. The pigments may be selected from organic pigment, inorganic pigment; or mixtures thereof. The pigments may be selected from coloured pigments; pearlescent pigments; or mixtures thereof. Said crosslinking and/or pretreatment composition may comprise from about 0.01% to 10%, or from about 1% to about 2% pigment present in the product mass in undissolved form by weight of the total crosslinking and/or pretreatment composition. The pretreatment and/or crosslinking composition may comprise pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water-soluble components such as those having C.I. Names.

In at least one embodiment, the cosmetic agent may be a particulate substance. In at least one embodiment, the particulate substance is selected from silica; silicates; aluminates; clay earths; mica; insoluble salts, particularly insoluble inorganic metal salts; metal oxides; minerals; insoluble polymer particles; or mixtures thereof. In at least one embodiment, the crosslinking and/or pretreatment composition comprises from about 0.01% to about 10%, or from about 0.05% to about 5% of at least one particulate substance. In at least one embodiment, the crosslinking and/or pretreatment composition is substantially free of a particulate substance such as clay.

In at least one embodiment, the cosmetic agent may be a preservative. In at least one embodiment, the crosslinking and/or pretreatment composition may comprise from about 0.01% to about 5% by weight, or from about 0.05% to about 1% preservative.

A variety of additional optional ingredients may be incorporated into the crosslinking and/or pretreatment composition of the present invention. Non-limiting examples of these additional ingredients may be selected from preservatives; antioxidants; sequestering agents; solvents; fragrances & perfumes; fillers; screening agents; odour absorbers; colouring materials; lipid vesicles; detersive surfactants; thickening agents and suspending agents; viscosity modifiers; pearlescent aids; UV-filters and sunscreens; agents for combating free radicals; polyvinyl alcohol; pH adjusting agents; salts; colouring agents; polymer plasticizing agents; direct dyes; or mixtures thereof. The crosslinking and/or pretreatment composition may comprise from about 0%, or from about 0.1% to about 5% antimicrobial agents. In at least one embodiment, the crosslinking and/or pretreatment composition comprises an organic acid selected from the group consisting of: glycine, L-methionine, L-arginine, biotin, creatine, and mixtures thereof. In at least one embodiment, the preatreatment and/or crosslinking composition comprises an antidandruff agent. In at least one embodiment, the pretreatment and/or crosslinking composition comprises zinc pyrithione. In at least one embodiment, the pretreatment and/or crosslinking composition comprises panthenol. In at least one embodiment, the pretreatment and/or crosslinking composition comprises a wax compound. In at least one embodiment, the pretreatment and/or crosslinking composition comprises beeswax.

In at least one embodiment, the crosslinking and/or pretreatment composition has a viscosity, measured at 25° C., of from about 0.1 mPa·s to about 1,000,000 mPas, or from about 1 mPa·s to about 80,000 mPa·s, or from about 5 mPa·s to about 3,500 mPa·s. The viscosity is measured by HAAKE Rotation Viscometer VT 550 with cooling/heating vessel and sensor systems according to DIN 53019 (MV-DIN, SV-DIN), shear rate is 12.9 $s^{-1}$.

In at least one embodiment, the preatreatment and/or crosslinking composition is substantially free of: formaldehyde, derivatives of formaldehyde, methylene glycol, formalin, and any compound that produces formaldehyde upon heating. "Heating" means raising the temperature of the compound above 25° C. In at least one embodiment, the crosslinking composition comprises 0% formaldehyde. In at least one embodiment, the derivatives of formaldehyde are 1,3,5-trioxane and paraformaldehyde. In at least one embodiment, the crosslinking composition is substantially free of: formaldehyde, 1,3,5-trioxane, paraformaldehyde, methylene glycol, formalin. Formaldehyde is not preferred in view of its safety profile. Formalin is not advantageous because formalin is a derivative of formaldehyde. Formaldehyde exists in multiple forms. In water, formaldehyde becomes hydrated and forms methylene glycol. A saturated solution of formaldehyde (about 40% formaldehyde) in water is more commonly known as formalin. Methanol and/or methylene diol can be used as a stabilizer in formalin and is therefore not advantageous. In at least one embodiment, the preatreatment and/or the crosslinking composition is substantially free of a quaternary ammonium compound and/or a surfactant. In at least one embodiment, the pretreatment and/or crosslinking composition is substantially free of: ceramide compound, an alpha-hydroxy acid, a thioglycolate and/or thiolactate compound, a bisulfate compound, clay, a reducing agent. In at least one embodiment, the pretreatment and/or crosslinking composition is substantially free of: ceramide compound, an alpha-hydroxy acid, a thioglycolate and/or thiolactate compound, a bisulfate compound. In at least one embodiment, the pretreatment and/or crosslinking composition is substantially free of a carbonate compound. In at least one embodiment, the pretreatment and/or crosslinking composition is substantially free of: ceramide compound, an alpha-hydroxy acid, a thioglycolate or thiolactate compound, a bisulfate compound, clay, formaldehyde, 1,3,5-trioxane, paraformaldehyde, methylene glycol, quaternary ammonium compound, surfactant.

Method

The method described herein comprises (a) providing and applying a pretreatment composition to keratin fibers; (b) leaving the pretreatment composition on the keratin fibers for a time period from about 5 min. to about 12 hours; (c) optionally rinsing and/or drying the keratin fibers; (d) providing and applying a crosslinking composition to the keratin fibers; (e) drying the keratin fibers; (f) providing a keratin fiber shaping appliance at a temperature of from about 50° C. to about 280° C. and mechanically shaping the hair with the appliance; (g) optionally rinsing the keratin fibers; wherein the method may not comprise a rinsing step between step (d) and step (f). The method steps are in the order (a), then (b), then optionally (c), then (d), then (e), then (f), then optionally (g). In the method described herein, the crosslinking composition and/or the pretreatment composition may be applied on wet keratin fibers or on dry keratin fibers.

It is not preferred to employ a rinsing step between step (d) and step (f) because less straightening durability may be observed. Indeed, it is believed that reduced penetration into the hair shaft exists when the the crosslinking composition is rinsed off prior to step (f).

In an embodiment, prior to step (a) the keratin fibers are washed with a shampoo, for example a cleansing shampoo. In an embodiment, following step (b) the keratin fibers are washed with a shampoo, for example a cleansing shampoo. In an embodiment, following step (b) the keratin fibers are washed with a shampoo, for example a cleansing shampoo, and subsequently conditioned with a conditioning formulation comprising a conditioning agent. Conditioning agents are disclosed herein and are suitable for this embodiment. In an embodiment, following step (b) the keratin fibers are washed with a shampoo and then conditioned with a conditioning formulation comprising a conditioning agent and then dried using a blow dryer and a brush. In an embodiment, the method comprises, prior to step a), providing keratin fibers that have already been straightened. Indeed, providing keratin fibers that have already been straightened has the advantage that the present treatment is relatively gentle and therefore highly suitable for hair that has been previously damaged by less gentle treatments. Consumers believe that where they have used e.g. a formaldehyde-based treatment previously, they cannot use another straightening treatment until the damage has grown out/been trimmed off. This is not the case for the present invention since it offers a semi-durable and gentle, yet efficacious straightening treatment that is highly suited to hair that has already been straightened.

In an embodiment, the method relates to a keratin fiber shaping method comprising: (a) providing and applying a pretreatment composition to keratin fibers, wherein the composition comprises from about 1% to about 20% of a pretreatment active agent selected from the group consisting of: maleic anhydride, maleic acid, citric acid, fumaric acid, and mixtures thereof; (b) leaving the pretreatment composition on the keratin fibers for a time period of about 5 minutes to about 24 hours; (c) optionally rinsing and/or drying the keratin fibers; (d) providing and applying a crosslinking composition to the keratin fibers; (e) drying the keratin fibers; (f) providing a keratin fiber shaping appliance at a temperature of from about 50° C. to about 280° C. and mechanically shaping the keratin fibers with the appliance; and (g) optionally rinsing the keratin fibers; wherein the composition is substantially free of: formaldehyde, derivatives of formaldehyde, methylene glycol, formalin, and any compound that produces formaldehyde upon heating; and wherein the composition has a pH of from about pH 6 to about pH 11; wherein the method does not comprise a rinsing step between step (a) and step (d); and wherein the method does not use any coating material; and optionally wherein the composition comprises a conditioning agent, and wherein the conditioning agent is an epoxyaminosilane copolymer.

In an embodiment, the invention relates to a method for shaping keratin fibers comprising: (a) providing and applying a pretreatment composition to keratin fibers; (b) leaving the pretreatment composition on the keratin fibers for a time period from about 5 min to about 12 hours; (c) optionally drying and/or rinsing the keratin fibers; (d) providing and applying a crosslinking composition to the keratin fibers; (e) drying the keratin fibers; (f) providing a keratin fiber shaping appliance at a temperature of from about 80° C. to about 100° C. and exposing the composition to electromagnetic radiation having a wavelength of from about 300 nm to about 750 nm; and (g) optionally rinsing the keratin fibers.

Applying a Pretreatment Composition to Keratin Fibers

The present invention relates to a method for shaping keratin fibers, wherein the method comprises (a) providing and applying a pretreatment composition to the keratin fibers; and (b) leaving the pretreatment composition on the keratin fibers. In one embodiment, applying the pretreatment composition to keratin fibers involves applying onto keratin fibers from about 0.01 gram to about 5 gram of said composition per gram keratin fiber. In one embodiment, the composition is applied to the keratin fiber for at least 2 minutes, or from about 5 minutes to about 24 hours, or from about 10 minutes to about 8 hours, or from about 20 minutes to about 4 hours, or from about 30 minutes to about 2 hours, prior to carrying out optional step c). In at least one embodiment, the pretreatment composition is applied prior to going to bed, and the pretreatment composition is left on the consumer's hair for at least about 8 hours and allowed to air dry. In at least one embodiment, the consumer may be provided a head covering for overnight treatment.

Applying a Crosslinking Composition to Hair

The present invention relates to a method for shaping keratin fibers comprising: (d) providing and applying a crosslinking composition to the keratin fibers. In an embodiment, applying a crosslinking composition involves applying onto keratin fibers from about 0.01 gram to about 5 gram of said composition per gram keratin fiber. In an embodiment, the composition is on the hair for at least 2 min, or from about 5 min to about 45 min, or from about 10 min to about 40 min, or from about 20 min to about 35 min, prior to carrying out step e).

Drying the Keratin Fibers

The present invention relates to a method for shaping keratin fibers comprising steps (c) optionally drying the keratin fibers; and step (e) drying the keratin fibers. In an embodiment, the keratin fiber drying is carried out by a blow drier. In an embodiment, the fiber drying is carried out for a duration of from about 1 min to about 45 min, or from about 2 min to 20 min, or from about 5 min to 15 min. In general, following the keratin fiber drying, the fibers can still be damp, but needs to have reasonable e.g. 75% fiber separation of the head of hair. Some residual moisture in the fibers is acceptable. In an embodiment, the fibers are not wetted or rinsed prior to step (f). A high level of moisture is not preferred in view of hair damage caused by steam during step (f). Thus, the keratin fiber drying step (e) provides a method with reduced hair damage versus conventional methods.

In an embodiment, the keratin fiber drying is carried out by a hood appliance. In an embodiment, the keratin fiber drying is carried out by towelling hair and/or by pressing hair with hands.

Hair dryer or blow dryer distances between device and head are typically down to about 10 cm. Blow dryers direct hot air through some sort of attachment for combing or otherwise treating the hair. A blow dryer is typically used such that the distance to the hair (for example at a distance of 20 or 30 or 40 centimeters) and often is used with the aid of a comb or a brush. In an embodiment, the hair drying is carried out by a blow drier at a temperature of from about from 50° C. to about 100° C. In an embodiment, the hair drying is carried out by a blow drier at a temperature of up to 130° C. In an embodiment, the keratin fiber drying in steps (c) or (e) is carried out with a blow drier with brushing to help straightening the hair.

In an embodiment, the drying may occur by air drying. The consumer may choose to leave the pretreatment composition on her head for at least about 1 hour, wherein the drying process occurs via air drying. In one embodiment, the pretreatment composition may be air dried when the composition is left on the hair for about 1 hour to about 24 hours, or from about 2 hours to about 11 hours, or from about 3 hours to about 10 hours, or from about 4 hours to about 9 hours, or from about 5 hours to about 8 hours, or from about 6 hours to about 7 hours.

Providing a Keratin Fiber Shaping Appliance and Mechanically Shaping the Keratin Fibers The present invention relates to a method for shaping keratin fibers comprising (f) providing a keratin fiber shaping appliance at a temperature from about 50° C. to about 280° C. and mechanically shaping the keratin fibers. In an embodiment, the temperature is from about 110° C. to about 250° C., or from about 120° C. to about 240° C., or from about 140° C. to about 230° C., or from about 160° C. to about 220° C., or from about 180° C. to about 210° C., or from about 190° C. to about 200° C.

The method uses an keratin fiber shaping appliance. In at least one embodiment, the appliance is a hair straightening appliance comprising a heating element. In at least one embodiment, the appliance is a hair curling appliance comprising a heating element. In at least one embodiment, the appliance is a hair straightening appliance comprising a heating element and a source of electromagnetic radiation for exposing hair to electromagnetic radiation. In at least one embodiment, the implement is a combing or brushing means and the crosslinking composition is exposed to electromagnetic radiation having a wavelength of from about 300 nm to about 750 nm using a separate source of electromagnetic radiation such as a lamp. In at least one embodiment, the appliance comprises light-emitting diodes.

In an embodiment, the the 'mechanically shaping the keratin fibers with the appliance' is carried out by a hair straightening appliance. In an embodiment, the hair straightening appliance comprises metal or ceramic plates. In an embodiment, the hair straightening appliance is a pair of straightening irons. Hair straightening appliances comprising metal or ceramic plates, such straightening irons typically rely on resistive heating, but heat is not transported through hot air, but by direct contact of the plates with the keratin fibres. The direct contact is often made by bringing the hair in contact with some metal or ceramic surface of the appliance. These devices typically are not or at least not primarily used to dry the hair. Rather are they used to change the hair style, typically either to create curls or to straighten hair. The surfaces meant for hair contact (e.g. metal or ceramic plates) of these devices typically reach temperatures from 130° C. to 250° C. Most devices have metal or ceramic plates used with temperatures from 160° C. to 230° C. U.S. Pat. Nos. 5,612,849 and 6,191,930, which are incorporated herein by reference, disclose a heat generating hair care appliance in the form of a hot air hair care appliance. The respective devices are typically referred to as hair dryers or blow dryers. U.S. Pat. No. 383,245, which is incorporated herein by reference, discloses another heat generating hair care appliance in the form of a hot air hair care appliance. The respective devices are typically referred to as hot air stylers or hair stylers. US2008/0196739, which is incorporated herein by reference, discloses a heat generating hair care appliance in the form of a hot surface hair care appliance, typically referred to as a straightening irons.

In at least one embodiment, the crosslinking composition is exposed to electromagnetic radiation having a wavelength of from about 300 nm to about 750 nm. In at least one embodiment, the electromagnetic radiation has a wavelength of from about 310 nm, or from about 320 nm, or from about 330 nm, or from about 340 nm, or from about 350 nm, or from about 360 nm, or from about 370 nm, or from about 380 nm, or from about 390 nm, or from about 400 nm, or from about 410 nm, to about 740 nm, or to about 730 nm, or to about 720 nm, or to about 710 nm, or to about 700 nm, or to about 690 nm, or to about 680 nm, or to about 670 nm, or to about 650 nm, or to about 640 nm. In at least one embodiment, the electromagnetic radiation has a wavelength of from 380 nm to about 550 nm.

Irradiance, that is the power of electromagnetic radiation in Watts per unit area, has the unit Watts per m$^2$ or W/m$^2$. Irradiance is thus a measurement of the intensity of electromagnetic radiation. Light intensity can also be measured in lux (lx), which is the unit of illuminance. 1 1x=about 1.5×10$^{-7}$ W/cm$^2$ (at 555 nm). An average laboratory or office space would have a light intensity of about 200 1x to about 1000 1x i.e. an irradiance of about 2.9×10$^{-5}$ W/cm$^2$ to about 1.4×10$^{-4}$ W/cm$^2$ (at 555 nm). In at least one embodiment, the electromagnetic radiation has an irradiance of at least about 1×10$^{-3}$ W/cm$^2$, or at least about 5×10$^{-3}$ W/cm$^2$, or at least about 1×10$^{-2}$ W/cm$^2$, or at least about 5×10$^{-2}$ W/cm$^2$, or at least about 1×10$^{-1}$ W/cm$^2$, or at least about 5×10$^{-1}$ W/cm$^2$. In at least one embodiment, the electromagnetic radiation has an illuminance of at least about 1000 1x, or at least about 2000 1x, or at least about 3000 1x, or at least about 4000 1x, or at least about 5000 1x, or at least about 6000 1x, or at least about 7000 1x, or at least about 8000 1x, or at least about 9000 1x, or at least about 10000 1x, or at least about 20000 1x, or at least about 30000 1x, or at least about 40000 1x, or at least about 50000 1x, or at least about 60000 1x, or at least about 70000 1x, or at least about 80000 1x.

In at least one embodiment, the electromagnetic radiation is selected from the group consisting of: ambient light, sunlight, incandescent light, fluorescent light, LED light, laser light, and combinations thereof. In at least one embodiment, the electromagnetic radiation is selected from the group consisting of: visible light, near or far ultraviolet light, or near or far infrared light, and combinations thereof. In at least one embodiment, the electromagnetic radiation is light. In at least one embodiment, the suitable light may be provided from any source capable of illuminating the substrate surface. In at least one embodiment, the light is selected from the group consisting of: ambient sunlight, incandescent light, and fluorescent light. In at least one embodiment, the light is provided by conventional sources such as lamps and portable or battery-powered lights. Specific devices may be developed or adapted for use with the crosslinking compositions and method described herein. In at least one embodiment, the appliance is a hair brush configured to incorporate LEDs In at least one embodiment, the light is laser light. Laser may be used to provide precise targeting, for example. In at least one embodiment, the appliance is hybrid heat and light providing hair straightening irons.

In an embodiment, the kearatin fiber shaping appliance comprises metal or ceramic plates. In an embodiment, the metal or ceramic plates are provided to a temperature of from about 50° C. to about 280° C. In an embodiment, the metal or ceramic plates are provided to a temperature of from about 110° C. to about 250° C., or from about 120° C. to about 240° C., or from about 140° C. to about 230° C., or from about 160° C. to about 220° C., or from about 180° C. to about 210° C., or from about 190° C. to about 200° C.

In an embodiment, the 'mechanically shaping the keratin fibers with the appliance' is carried out for a duration of from about 1 min to about 45 min, or from about 2 min to 20 min, or from about 5 min to 15 min. In an embodiment, the 'mechanically shaping the keratin fibers with the appliance' is carried out for a duration of for at least 10 min, or for at least 12 min.

In an embodiment, the hair straightening and/or hair relaxing regimen comprises the method according to any of the preceding paragraphs, wherein the complete method (a) to (f) is repeated at least 3 times at a frequency of at least once every 48 hours. In an embodiment, the complete method (a) to (f) is repeated at least 2 times at a frequency of at least once every 24 hours. In an embodiment, the complete method (a) to (f) is repeated at least 5 times at a frequency of at least once every 48 hours, or once every 24 hours.

In an embodiment, a kit for straightening hair comprises: (i) a pretreatment composition; (ii) a crosslinking composition; and (iii) a heating device comprising a flat iron. In an embodiment, the kit is for perming and/or curling hair. In an embodiment, the kit is for semi-permanent shaping of hair.

In an embodiment, a kit for straightening hair comprises: (i) a pretreating and a crosslinking composition; (ii) a heating device comprising a flat iron at a temperature of from about 80° C. to about 100° C. and capable of providing electromagnetic radiation having a wavelength of from about 300 nm to about 750 nm. In an embodiment, the kit is for perming and/or curling hair. In an embodiment, the kit is for semi-permanent shaping of hair.

EXAMPLES

The following examples further describe and demonstrate embodiments within the scope of the present invention. The examples are given solely for the purpose of illustration, and are not to be construed as limitations of the present invention since many variations thereof are possible without departing from its scope.

Example Pre-Treatment Compositions

Liquid A:
5 g maleic anhydride, 2 g epoxyaminosilane copolymer, QSP water

Liquid B:
5 g maleic acid, 1 g epoxyaminosilane copolymer, QSP water.

Liquid C:
5 g maleic anhydride, 2 g epoxyaminosilane copolymer, pH4 buffer (buffer is phosphate or), QSP water.

Liquid Gel:
5 g maleic anhydride, 1.00 g Luviset Clear, 1.50 g surfactant 193, 0.30 g Carbomer, 0.30 g aminomethylpropanol (aka AMP) 95%, 0.20 g Emulgin L, 0.15 g perfume, 0.40 g Natrosol G, 16.50 g ethanol, QSP water.

Rapid Drying Gel:
5 g maleic anhydride, 1.00 g Luviset Clear, 1.80 g Polyvinylpyrrolidone K 90; 1.00 g direct dye; 1.50 g surfactant 193; 1.00 g Synthalen W 2000; 0.30 g AMP (95%); 0.30 g PEG-25 PABA (Uvinul P 25); 0.15 g Panthenol; 0.30 g perfume; 34.20 g ethanol; 0.10 g keratin hydrolysate; QSP water.

Pump, Setting Foam:
5 g citric acid, 1.80 g Luviset Clear, 1.90 g direct dye, 0.40 g Cocamidopropyl Hydroxysultaine, 0.10 g Rosemary leaf extract (Extrapon Rosemary), 8.90 g ethanol, 0.10 g Extrapon seven herbs—extract, 0.10 g Panthenyl ethyl ether, 0.15 g Perfume, QSP water. The composition is packaged in a packaging with mechanically operated pump foaming device.

Aerosol—Setting Foam—Extra Strong Hold:
4 g maleic anhydride, 2.10 g Luviset Clear, 0.60 g Vinyl acetate/crotonic acid copolymer, 0.50 g Polyquaternium-7, 4.00 g butane, 4.00 g propane, 8.90 g ethanol 510, 0.40 g PEG-25 PABA, 0.20 g Panthenol, 0.20 g perfume, 0.20 g Laureth-4, 0.07 g C9-C11 Pareth-8, QSP 100.00 g water. The composition is bottled in an aerosol can with foaming head.

Setting Spray:
10 g maleic anhydride, 1.00 g Luviset Clear, 0.65 g Octylacrylamide/Acrylates/Butylaminoethylmethacrylate Copolymer (Amphomer), 0.20 g Celquat L200, 28.5 g ethanol, 0.60 g aminomethylpropanol 95%, 0.25 g perfume, 0.20 g Cetyltrimethylammonium chloride, QSP 60.00 g water. The composition is bottled in a packaging with pump spray device.

Rinse-Out Conditioner:
20 g maleic anhydride, 1.00 g cetyltrimethyl ammonium chloride, 1.00 g polymethylphenyl siloxane, 0.40 g phenoxy ethanol, 0.20 g PHB-methylester, 1.00 g Dow Corning 949 Cationic Emulsion®, 5.00 g isododecane, 0.40 g perfume oil, QSP water.

Rinse-Out Conditioner:
20 g maleic acid, 1.00 g cetyltrimethyl ammonium chloride, 1.00 g polymethylphenyl siloxane, 0.40 g phenoxyethanol, 0.20 g PHB-methylester, 8.00 g Dow Corning 57113 Cationic Emulsion®, 5.00 g isododecane, 0.40 g perfume oil, QSP water.

Leave-in Conditioner: 2 g maleic acid, 1.00 g cetyltrimethyl ammonium chloride, 1.00 g polymethylphenyl siloxane, 0.40 g phenoxy ethanol, 0.20 g PHB-methylester, 8.00 g Momentive™ Cationic Emulsion®, 5.00 g isododecane, 0.40 g perfume oil, QSP water.

Leave-in Conditioner:
2 g fumaric acid, 0.10 g vitamin E-acetate, 0.50 g polymethylphenyl siloxane, 10.00 g propylene glycol, 0.50 g behenyl trimethylammonium chloride, 0.05 g sodium chloride, 0.30 g d-panthenol, 0.30 g PHB-propylester, 2.00 g isododecane, 0.20 g perfume oil, QSP water.

Shampoo:
2 g maleic acid, 0.20 g Jaguar C-162, 40.00 g sodium laureth sulfate (LES 28%), 5.00 g Cocamidopropyl betaine, 2.00 g Dow Corning 200 Fluid/350 CS, 0.15 g perfume, QSP water.

Example Crosslinking Compositions

Liquid A:
15 g glyoxylic acid, 2 g epoxyaminosilane copolymer, QSP water

Liquid B:
10 g 1,3-dioxane-2-one, 1 g epoxyaminosilane copolymer, 0.1 g NaOH, QSP water.

Liquid C:
5 g ribose, 2 g epoxyaminosilane copolymer, pH10 buffer (buffer is borate or carbonate), QSP water.

Liquid Gel:
12.00 g ethylene carbonate; 1.00 g Luviset Clear, 1.50 g surfactant 193, 0.30 g Carbomer, 0.30 g aminomethylpropanol (aka AMP) 95%, 0.20 g Emulgin L, 0.15 g perfume, 0.40 g Natrosol G, 16.50 g ethanol, QSP water.

Rapid Drying Gel:
12.00 g arabinose, 1.00 g Luviset Clear, 1.80 g Polyvinylpyrrolidone K 90; 1.00 g direct dye; 1.50 g surfactant 193; 1.00 g Synthalen W 2000; 0.30 g AMP (95%); 0.30 g PEG-25 PABA (Uvinul P 25); 0.15 g Panthenol; 0.30 g perfume; 34.20 g ethanol; 0.10 g keratin hydrolysate; QSP water.

Pump, Setting Foam:
10.00 g 1,2-bis(2-maleimidoethoxy)ethane, 1.80 g Luviset Clear, 1.90 g direct dye, 0.40 g Cocamidopropyl Hydroxysultaine, 0.10 g Rosemary leaf extract (Extrapon Rosemary), 8.90 g ethanol, 0.10 g Extrapon seven herbs—extract, 0.10 g Panthenyl ethyl ether, 0.15 g Perfume, QSP water. The composition is packaged in a packaging with mechanically operated pump foaming device.

Aerosol—Setting Foam—Extra Strong Hold:
8.00 g citric acid, 2.10 g Luviset Clear, 0.60 g Vinyl acetate/crotonic acid copolymer, 0.50 g Polyquaternium-7, 4.00 g butane, 4.00 g propane, 8.90 g ethanol 510, 0.40 g PEG-25 PABA, 0.20 g Panthenol, 0.20 g perfume, 0.20 g Laureth-4, 0.07 g C9-C11 Pareth-8, QSP 100.00 g water. The composition is bottled in an aerosol can with foaming head.

Setting Spray:
10.2 g pyruvic acid, 1.00 g Luviset Clear, 0.65 g Octylacrylamide/Acrylates/Butylaminoethylmethacrylate Copolymer (Amphomer), 0.20 g Celquat L200, 28.5 g ethanol, 0.60 g aminomethylpropanol 95%, 0.25 g perfume, 0.20 g Cetyltrimethylammonium chloride, QSP 60.00 g water. The composition is bottled in a packaging with pump spray device.

Rinse-Out Conditioner:
9.30 g 3-(2-hydroxyethyl)-2-oxazolidinone, 1.00 g cetyltrimethyl ammonium chloride, 1.00 g polymethylphenyl siloxane, 0.40 g phenoxy ethanol, 0.20 g PHB-methylester, 1.00 g Dow Corning 949 Cationic Emulsion®, 5.00 g isododecane, 0.40 g perfume oil, QSP water.

Rinse-Out Conditioner:
9.30 g 1,7-diaminoheptane, 1.00 g cetyltrimethyl ammonium chloride, 1.00 g polymethylphenyl siloxane, 0.40 g phenoxyethanol, 0.20 g PHB-methylester, 8.00 g Dow Corning 57113 Cationic Emulsion®, 5.00 g isododecane, 0.40 g perfume oil, QSP water.

Leave-in Conditioner:
9.30 g 1,4-butanediol, 1.00 g cetyltrimethyl ammonium chloride, 1.00 g polymethylphenyl siloxane, 0.40 g phenoxy ethanol, 0.20 g PHB-methylester, 8.00 g Momentive™ Cationic Emulsion®, 5.00 g isododecane, 0.40 g perfume oil, QSP water.

Leave-in Conditioner:
9.30 g xylose, 0.10 g vitamin E-acetate, 0.50 g polymethylphenyl siloxane, 10.00 g propylene glycol, 0.50 g behenyl trimethylammonium chloride, 0.05 g sodium chloride, 0.30 g d-panthenol, 0.30 g PHB-propylester, 2.00 g isododecane, 0.20 g perfume oil, QSP water.

Shampoo:
0.20 g Jaguar C-162, 40.00 g sodium laureth sulfate (LES 28%), 5.00 g Cocamidopropyl betaine, 2.00 g Dow Corning 200 Fluid/350 CS, 0.15 g perfume, 4.30 g xylose, 4.30 g arabinose, QSP water.

Further compositions disclosed in the European patent application 08151246.9 filed on 11 February 2008 referenced as examples 2 to 7, 9 to 17, 19 to 21, 23, 24, 26 to 35, 37, 39 to 45, and 46—which are incorporated herewith by reference—are also suitable as a chassis for the composition according to the present invention.

The trade names/raw materials used in the examples are: Abilquat 3270 (Quaternium-80, 50% in propylene glycol) from Goldschmidt; Aculyn 48 (PEG-150/stearyl alcohol/SMDI copolymer, 19% in water) from Rohm and Haas; AMP 95% (aminomethylpropanol, 95% aqueous solution); Amphomer (octylacrylamide/acrylates/butylaminoethyl-methacrylate copolymer); Aristoflex AVC (Ammonium Acryloyldimethyltaurate/VP copolymer); Aquaflex FX-64 (isobutylene/ethylmaleimide/hydroxyethylmaleimide copolymer, 40% strength in water/ethanol) from ISP; Aquaflex SF 40 (VP/vinyl caprolactam//DMAPA acrylates copolymer, 40% in ethanol) from ISP; Advantage S (vinyl caprolactam/VP/dimethylaminoethyl methacrylate copolymer); Carbomer—Carbopol (acrylic acid homopolymer); Celquat L200 (copolymer of hydroxyethylcellulose and diallyldimethyl-ammonium chloride; Polyquaternium-4); GENAMIN CTAC 50 (cetrimonium chloride; cetyltrimethylammonium chloride); Copolymer 845 (VP/Ddimethylaminoethylmethacrylate copolymer, 20% in water) from ISP; Dehydol LS 4 (Lauryl alcohol tetraoxyethylen ether); Dekaben LMB (iodopropynyl butylcarbamate, 10% strength in butylene glycol); Dekaben LMP (Phenoxyethanol and iodopropynyl butylcarbamate); Diaformer Z-711 (acrylates/lauryl acrylate/stearyl acrylate/ethylamine oxide methacrylate copolymer, 40%) from Clariant; Dow Corning 1401 (High molecular weight Dimethiconol, 13% in cyclomethicone); Eumulgin L (PEG-1-PEG-9 lauryl glycol ether; Flexan (Sodium polystyrene sulfonate); GAFQUAT 755 N (Polyquaternium-11); Jaguar C-17/162 (guar hydroxylpropyltrimonium chloride) Laureth-4 (Lauryl alcohol tetraoxyethylen ether); Luviset Clear (Terpolymer of vinylpyrrolidone, methacrylamide and vinylimidazole) from BASF; Luviskol VA 64 (vinylpyrrolidone/vinylacetate copolymer); Luviskol K 90 Powder (vinylpyrrolidone); Luvimer 100 P (t-butyl acrylate/ethyl acrylate/methacrylic acid copolymer); Natrosol G (hydroxyethylcellulose); Pemulen (acrylates/C10-30 alkyl acrylate crosspolymer); Structure 3001 (acrylates/ceteth-20 itaconate copolymer, 30% strength in water) from National Starch; Surfactant 193 (Ethoxylated dimethylpolysiloxane) from Dow Corning); Synthalen W 2000 (acrylates/palmeth-25 acrylate copolymer, 31% in water); Tego Betain L 5045 (cocamidopropyl betaine).

DATA

Referring to Table 1, it is found that pre-treating the hair with a pre-treatment formulation comprising maleic anhydride before the application of a cross-linking composition improves the durability of the cross-linking composition when used for straightening the hair. The tested pre-treatment formulation is detailed in Table 2 and comprises 5% maleic anhydride at a pH of 4 (pH was buffered with citric acid buffer). The cross-linking formulation applied after the pre-treatment formulation is detailed in Table 3. Table 4 provides further data illustrating the improved durability associated with pre-treating the hair with the pre-treatment formulation before the application of the cross-linking composition.

TABLE 1

| Level | | | | | Mean |
|---|---|---|---|---|---|
| Pre-treatment 24 hrs | A | | | | 6.33 |
| Pre-treatment 30 min | | B | | | 5.67 |
| Pre-treatment 15 min | | | C | | 5.00 |
| Without Pre-treatment | | | | D | 4.33 |
| Pre-treatment 10 min | | | | D | E | 4.00 |
| Pre-treatment 5 min | | | | | E | 3.67 |

*Levels not connected by the same letter are significantly different. Statistical analysis was done at the 89% confidence level.

TABLE 2

| Ingredient | Wt. % |
|---|---|
| Maleic Anhydride | 5 |
| pH 4 buffer (VWR)[1] | QS to 100 |

[1]BDH pH 4 buffer, manufactured by VWR. Citric acid 0.634 g and sodium citrate 0.439 g per 100 g solution.

TABLE 3

| Ingredient | Wt. % |
|---|---|
| Arabinose | 10 |
| Ethylene carbonate | 5 |
| pH 10 carbonate buffer (VWR)[1] | QS to 100 |

[1]BDH pH 10 buffer, manufactured by VWR. Sodium bicarbonate 0.42 g and sodium carbonate 1.431 g per 100 g solution.

TABLE 4

| Level | | | Mean |
|---|---|---|---|
| Pre-treatment 30 min | A | | 5.67 |
| Without MA | | B | 4.33 |
| Post-treatment 30 min | | B | 4.00 |

*Levels not connected by the same letter are significantly different. Statistical analysis was done at the 89% confidence level.

Test Method

Switches of low lift naturally curly hair are employed. These are shampooed with a Pantene clarifying shampoo to ensure the hair is in a clean state with no residues that could affect the end result. The switches are then rinsed. Excess water is removed from the hair by wringing out the switches. The switches are treated with a pretreatment composition.

The pretreatment composition comprises the ingredients set forth in Table 2. The ingredients are mixed on a spinner plate for 30 minutes prior to application. 0.25 g of pretreatment composition per 1 g hair is employed. The pretreatment composition is left on the hair for 30 minutes or as listed in Table 1.

The crosslinking composition is then applied to the hair. The crosslinking composition comprises the ingredients set forth in Table 3. The ingredients are mixed on a spinner plate for 30 minutes prior to application. 0.25 g of crosslinking composition per 1 g hair is employed. The crosslinking composition is left on the hair for 30 minutes. After this time, the hair is blow dried and brushed. The switches are then mechanically straightened with a flat iron (at 450° F. [232° C.]) with 8 passes. To simulate durability, the switches are then given one wash-and-dry cycle. One wash-and-dry cycle involves shampooing with a Hairtrition shampoo (Hairtrition Color Protect sulfate-free shampoo from Zotos), rinsing and then drying in a hot box. Once dry, the switches are then given 9 further wash-and-dry cycles.

Once dry, the switches are then imaged. An expert grader gives the images of the switches a score on a 0-10 scale. The scale is a standard scale. Curly hair having 4-5 nodes of curls is a score of 0 and very straight hair is a 10. Thus, the switches are compared to a normal state of hair. Using an expert grader is reliable because the grader is trained on measuring/scaling the configuration of the hair from straight to curly in a consistent way. Numeric data obtained by this method is averaged, and statistical analysis is conducted using JMP statistical software available from the SAS Institute at the 89% confidence level. Treatments not containing the same significance grouping letter are significantly different. For example, in Table 1 the pretreatment of 24 hours containing the letter "A" is considered significantly different than the 30 minute pretreatment containing the letter "B". Each level was repeated three times, and the mean value of the scores was reported.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or patent publication, is hereby incorporated herein by reference in its entirety unless expressly excluded or otherwise limited. The citation of any document is not an admission that it is prior art with respect to any document disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for shaping keratin fibres to achieve a semi-permanent hairstyle or semi-permanent shaping of eyelashes comprising:
   (a) providing a pretreatment composition comprising from about 4% to about 6%, by weight of the pretreatment composition, of a pretreatment active selected from the group consisting of maleic anhydride, maleic acid, and combinations thereof;
      wherein the pretreatment composition comprises a pH from about 4 to about 6;
   (b) applying the pretreatment composition to keratin fibres;
   (c) leaving the pretreatment composition on the keratin fibres for a time period from about 15 minutes to about 24 hours;
   (d) providing a crosslinking composition comprising:
      from about 9% to about 11% arabinose, by weight of the crosslinking composition;
      from about 4% to about 6% ethylene carbonate, by weight of the crosslinking composition;
      a cosmetically acceptable carrier;
   (e) applying the crosslinking composition to keratin fibres; and
   (f) mechanically shaping the keratin fibres with an appliance at a temperature of from about 50° C. to about 280° C.

2. The method according to claim 1, wherein the mechanical shaping of keratin fibres is straightening keratin fibres.

3. The method according to claim 1, wherein the method comprises leaving the pretreatment composition on the keratin fibres for a time period from about 25 minutes to about 24 hours.

4. The method according to claim 1, wherein the method comprises leaving the pretreatment composition on the keratin fibres for a time period from about 30 minutes to about 24 hours.

5. The method according to claim 1, wherein the crosslinking composition further comprises a photocatalyst.

6. The method according to claim 1, wherein arabinose and ethylene carbonate have a weight ratio of from about 7:4 to about 9:4.

7. The method according to claim 1, wherein the crosslinking composition further comprises a conditioning agent being the reaction product of an aminosilane and a polysiloxane.

8. The method according to claim 1, wherein the crosslinking composition is substantially free of the group consisting of formaldehyde, derivatives of formaldehyde, formalin, and any compound that produces formaldehyde upon heating.

9. The method according to claim 1, wherein the method does not comprise a rinsing step.

10. The method according to claim 1, wherein the crosslinking composition further comprises 1,2-bis(2-maleimidoethoxy)ethane.

11. A method for shaping keratin fibres to achieve a semi-permanent hairstyle or semi-permanent shaping of eyelashes comprising:
   a. providing a pretreatment composition comprising about 5%, by weight of the pretreatment composition, of a pretreatment active selected from the group consisting of maleic anhydride, maleic acid, and combinations thereof;
      wherein the pretreatment composition comprises a pH from about 5 to about 6;

b. applying the pretreatment composition to keratin fibres;
c. leaving the pretreatment composition on the keratin fibres for a time period from about 15 minutes to about 24 hours;
d. providing a crosslinking composition comprising:
   about 10% arabinose, by weight of the crosslinking composition;
   about 5% ethylene carbonate, by weight of the crosslinking composition;
   a cosmetically acceptable carrier;
e. applying the crosslinking composition to keratin fibres; and
f. mechanically shaping the keratin fibres with an appliance at a temperature of from about 50° C. to about 280° C.

12. A method for improving durability of a crosslinking composition when the crosslinking composition is used to straighten keratin fibres:
   a. providing a pretreatment composition comprising a pretreatment active selected from the group consisting of maleic anhydride, maleic acid, and combinations thereof;
   wherein the pretreatment composition comprises a pH from about 4 to about 6;
   b. providing a crosslinking composition comprising:
      from about 1% to about 20%, by weight of the crosslinking composition, of one or more protein crosslinking agents comprising arabinose and ethylene carbonate; and
      a cosmetically acceptable carrier;
   c. applying the pretreatment composition to keratin fibres, wherein the keratin fibers comprise keratin proteins inside the keratin fibres;
   d. then leaving the pretreatment composition on the keratin fibres for a time period from about 5 minutes to about 24 hours;
   e. after leaving the pretreatment composition on the keratin fibres, applying the crosslinking composition to the keratin fibres, wherein the crosslinking composition penetrates the keratin fibres and causes the keratin proteins to crosslink; and
   f. mechanically straightening the keratin fibres with an appliance at a temperature of from about 50° C. to about 280° C. to shape the keratin fibres and achieve a semi-permanent straight hairstyle;
   wherein the semi-permanent straight hairstyle is retained after five shampoo treatments.

13. The method according to claim 12, wherein the semi-permanent straight hairstyle is retained after ten shampoo treatments.

14. The method according to claim 1, wherein the pH of the pretreatment composition is from about 5 to about 6.

15. The method according to claim 12, wherein the pH of the pretreatment composition is from about 5 to about 6.

* * * * *